(12) United States Patent
Matsuda et al.

(10) Patent No.: US 10,765,485 B2
(45) Date of Patent: Sep. 8, 2020

(54) MEDICAL SUPPORT ARM DEVICE AND METHOD OF CONTROLLING MEDICAL SUPPORT ARM DEVICE

(71) Applicant: SONY CORPORATION, Tokyo (JP)

(72) Inventors: Yasuhiro Matsuda, Tokyo (JP); Tetsuharu Fukushima, Tokyo (JP); Yasuhisa Kamikawa, Tokyo (JP); Atsushi Miyamoto, Kanagawa (JP); Wataru Kokubo, Tokyo (JP)

(73) Assignee: SONY CORPORATION, Tokyo (JP)

( * ) Notice: Subject to any disclaimer, the term of this patent is extended or adjusted under 35 U.S.C. 154(b) by 457 days.

(21) Appl. No.: 15/541,052

(22) PCT Filed: Mar. 4, 2016

(86) PCT No.: PCT/JP2016/001198
§ 371 (c)(1),
(2) Date: Jun. 30, 2017

(87) PCT Pub. No.: WO2016/152046
PCT Pub. Date: Sep. 29, 2016

(65) Prior Publication Data
US 2018/0021094 A1    Jan. 25, 2018

(30) Foreign Application Priority Data

Mar. 23, 2015 (JP) ................................. 2015-060166
Oct. 23, 2015 (JP) ................................. 2015-208535

(51) Int. Cl.
*A61B 34/30*        (2016.01)
*A61B 90/00*        (2016.01)
(Continued)

(52) U.S. Cl.
CPC .............. *A61B 34/30* (2016.02); *A61B 90/36* (2016.02); *A61B 90/50* (2016.02);
(Continued)

(58) Field of Classification Search
CPC ......... A61B 34/30; A61B 34/74; A61B 90/36; A61B 90/50; A61B 1/00149
See application file for complete search history.

(56) References Cited

U.S. PATENT DOCUMENTS 6,786,896 B1    9/2004 Madhani et al.
2005/0043718 A1    2/2005 Madhani et al.
(Continued)

FOREIGN PATENT DOCUMENTS

JP        2010-188471 A        9/2010
JP        2011-206312 A        10/2011
(Continued)

OTHER PUBLICATIONS

Office Action issued in Japanese Application 2015-208535 dated Sep. 10, 2019.
(Continued)

*Primary Examiner* — Aaron B Fairchild
(74) *Attorney, Agent, or Firm* — Xsensus LLP

(57) ABSTRACT

There is provided a medical support arm device including a multi-joint arm having a distal end configured to host a medical device, said multi-joint arm configured to have a higher degree of freedom than a degree of freedom necessary for controlling a spatial position and pointing direction of the medical device. The multi-joint arm is configured to controllably displace at least one of a plurality of joints of the multi-joint arm while the spatial position and the pointing direction of the medical device are controlled.

21 Claims, 13 Drawing Sheets

(51) Int. Cl.
  *A61B 90/50* (2016.01)
  *A61B 34/00* (2016.01)
  *A61B 1/00* (2006.01)

(52) U.S. Cl.
  CPC .......... *A61B 1/00149* (2013.01); *A61B 34/74* (2016.02); *A61B 90/361* (2016.02); *A61B 2034/743* (2016.02); *A61B 2034/744* (2016.02)

(56) References Cited

U.S. PATENT DOCUMENTS

| | | |
|---|---|---|
| 2009/0012534 A1 | 1/2009 | Madhani et al. |
| 2009/0030429 A1 | 1/2009 | Madhani et al. |
| 2010/0069920 A1 | 3/2010 | Naylor et al. |
| 2011/0245844 A1 | 10/2011 | Jinno |
| 2012/0143212 A1 | 6/2012 | Madhani et al. |
| 2012/0158017 A1 | 6/2012 | Naylor et al. |
| 2013/0325032 A1* | 12/2013 | Schena .................. A61B 34/37 606/130 |
| 2014/0067117 A1 | 3/2014 | Orita |
| 2014/0107666 A1 | 4/2014 | Madhani et al. |
| 2016/0100900 A1 | 4/2016 | Madhani et al. |

FOREIGN PATENT DOCUMENTS

| | | |
|---|---|---|
| WO | 2010/030463 A1 | 3/2010 |
| WO | 2015/046081 A1 | 4/2015 |

OTHER PUBLICATIONS

International Search Report dated May 20, 2016, in PCT/JP2016/001198, filed Mar. 4, 2016.
Office Action dated Sep. 5. 2018 in corresponding European Patent Application No. 16 713 114.3, 4 pages.

* cited by examiner

[Fig. 1]
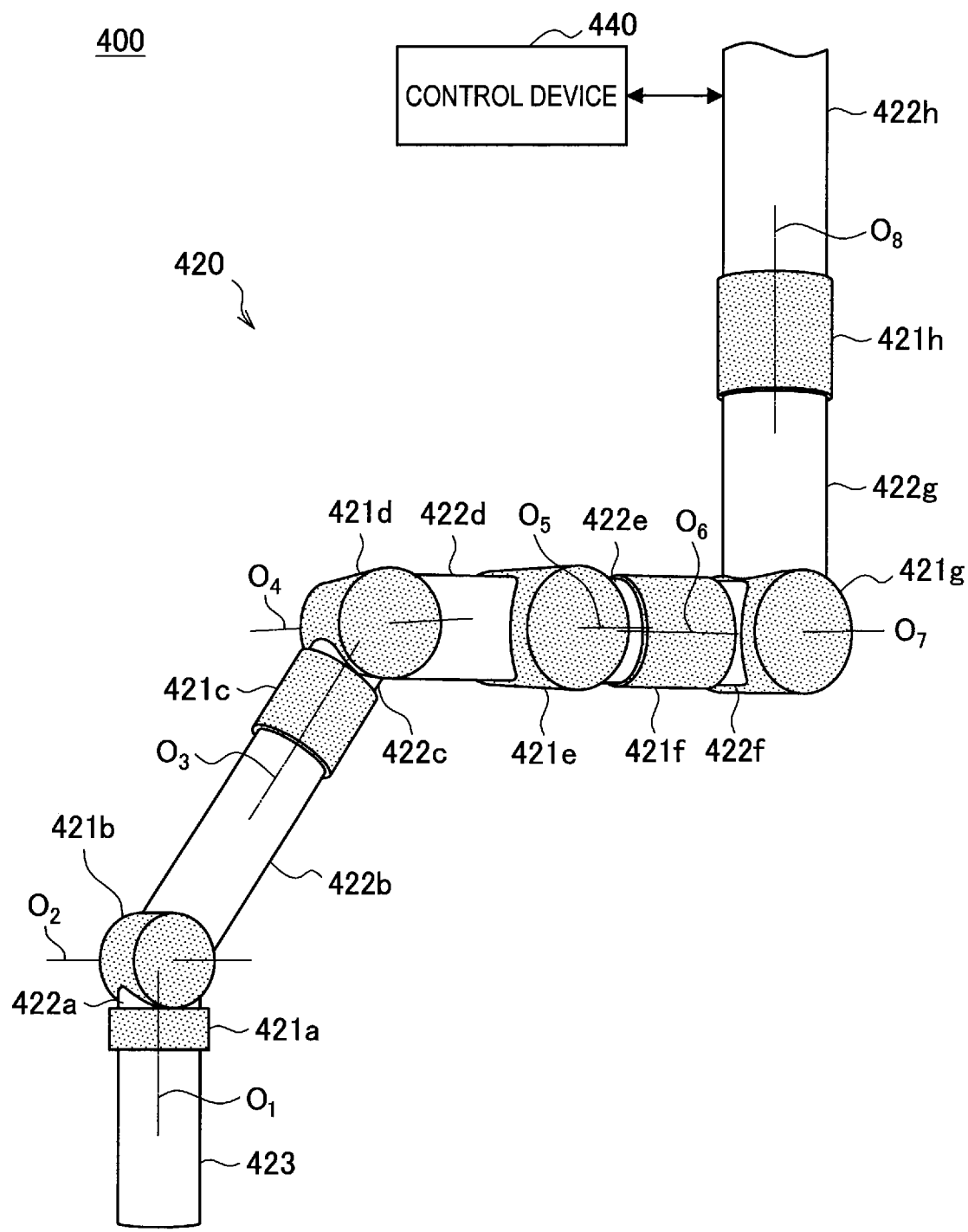

[Fig. 2]
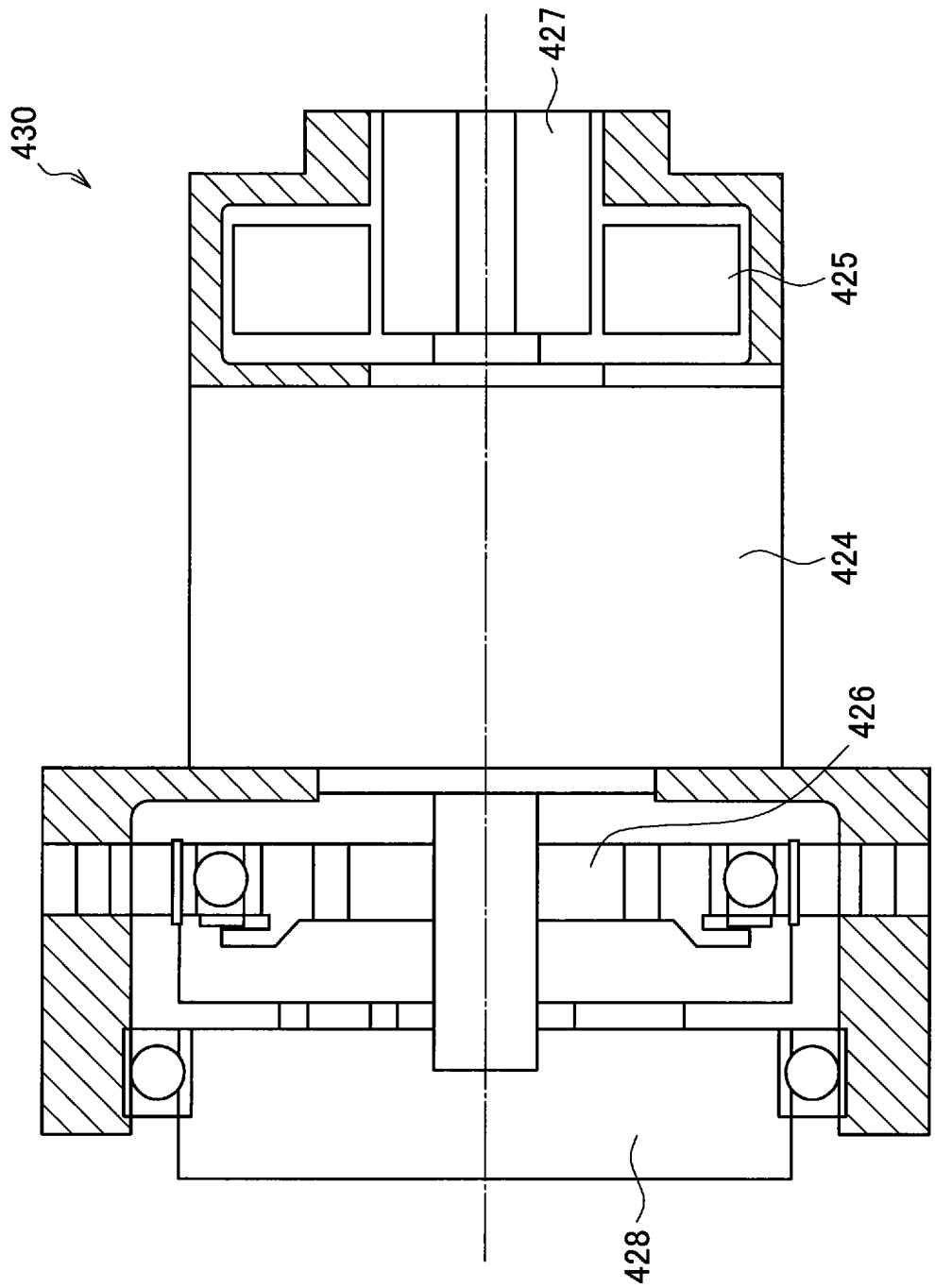

[Fig. 3]
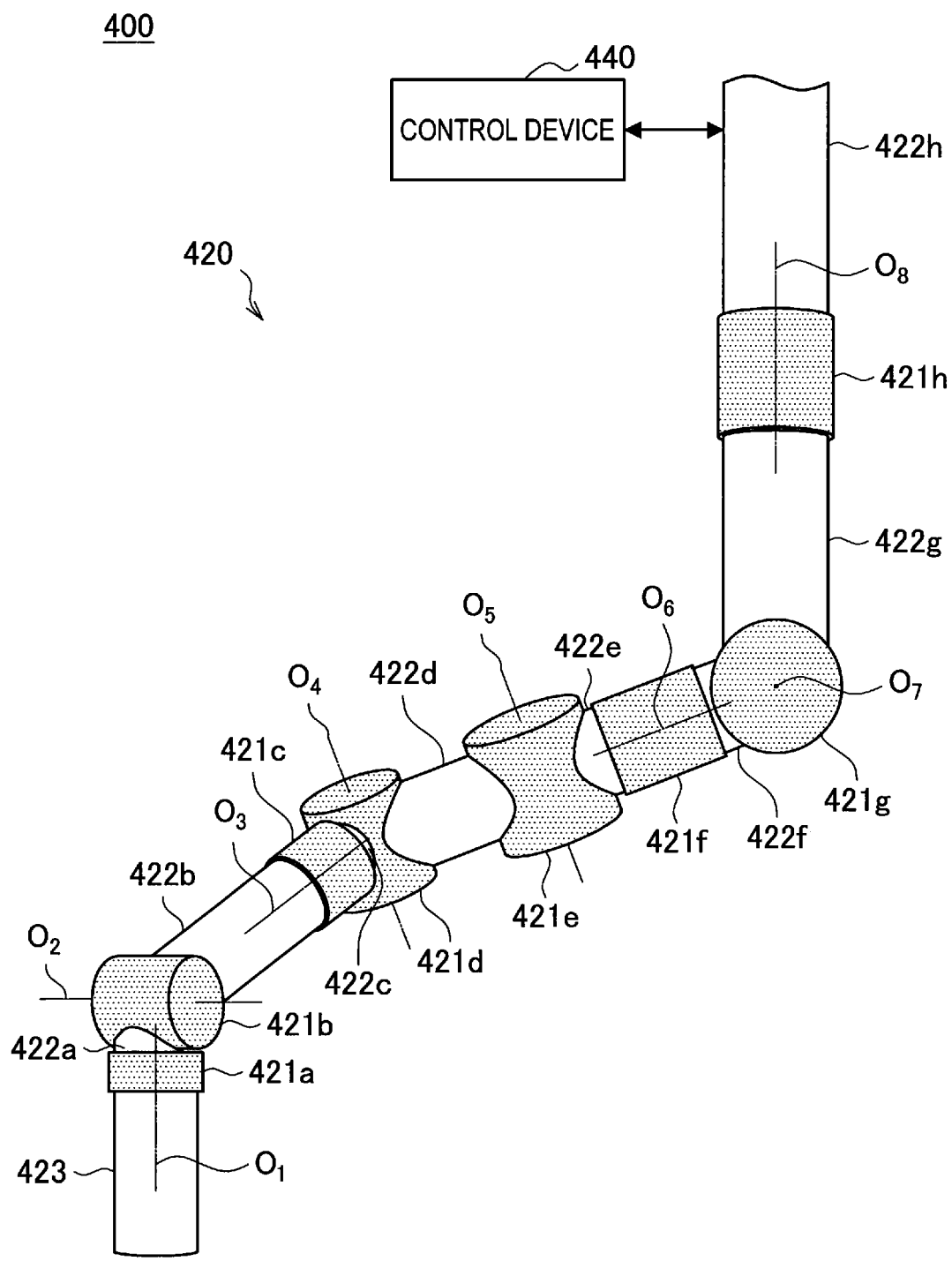

[Fig. 4]
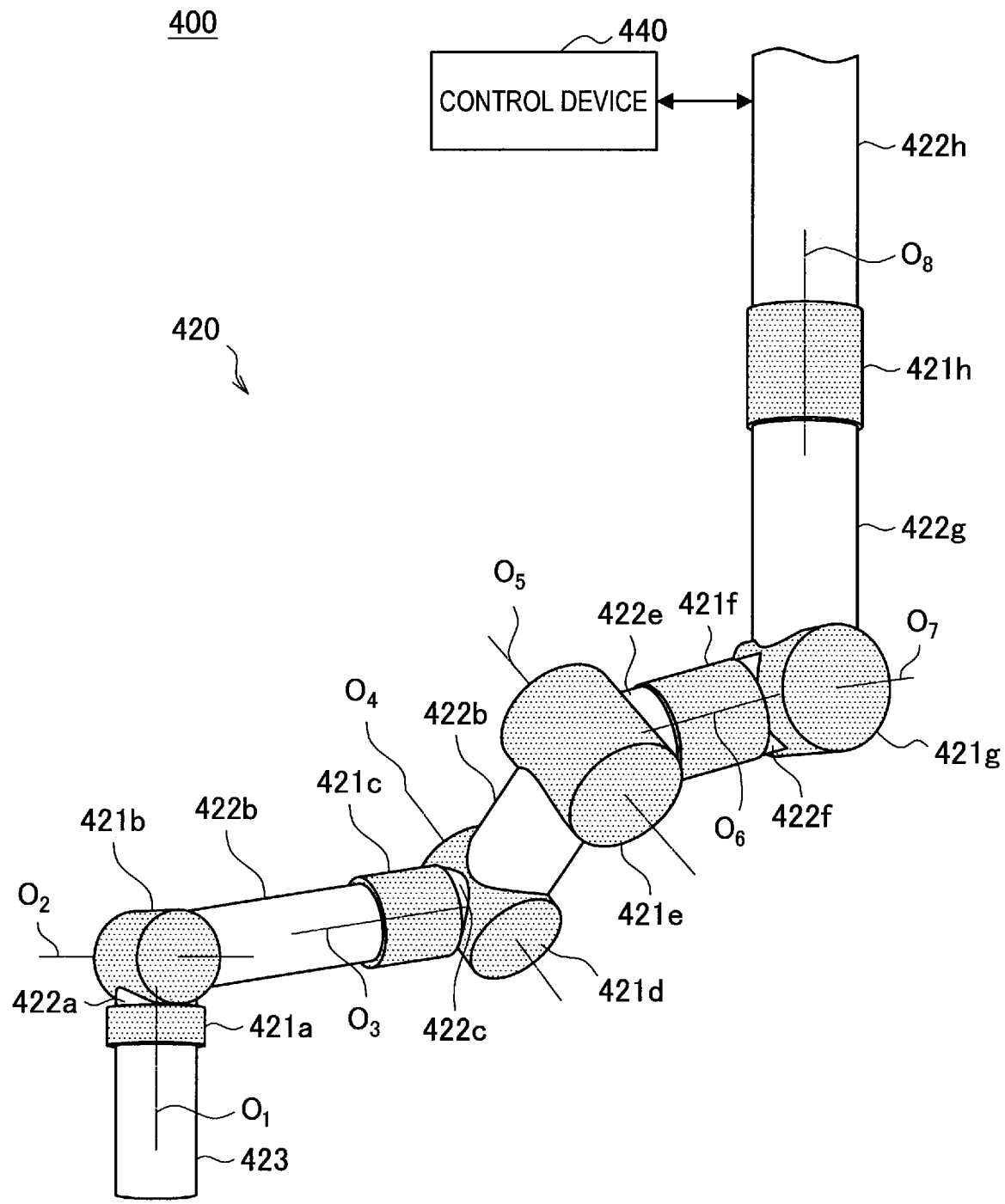

[Fig. 5]
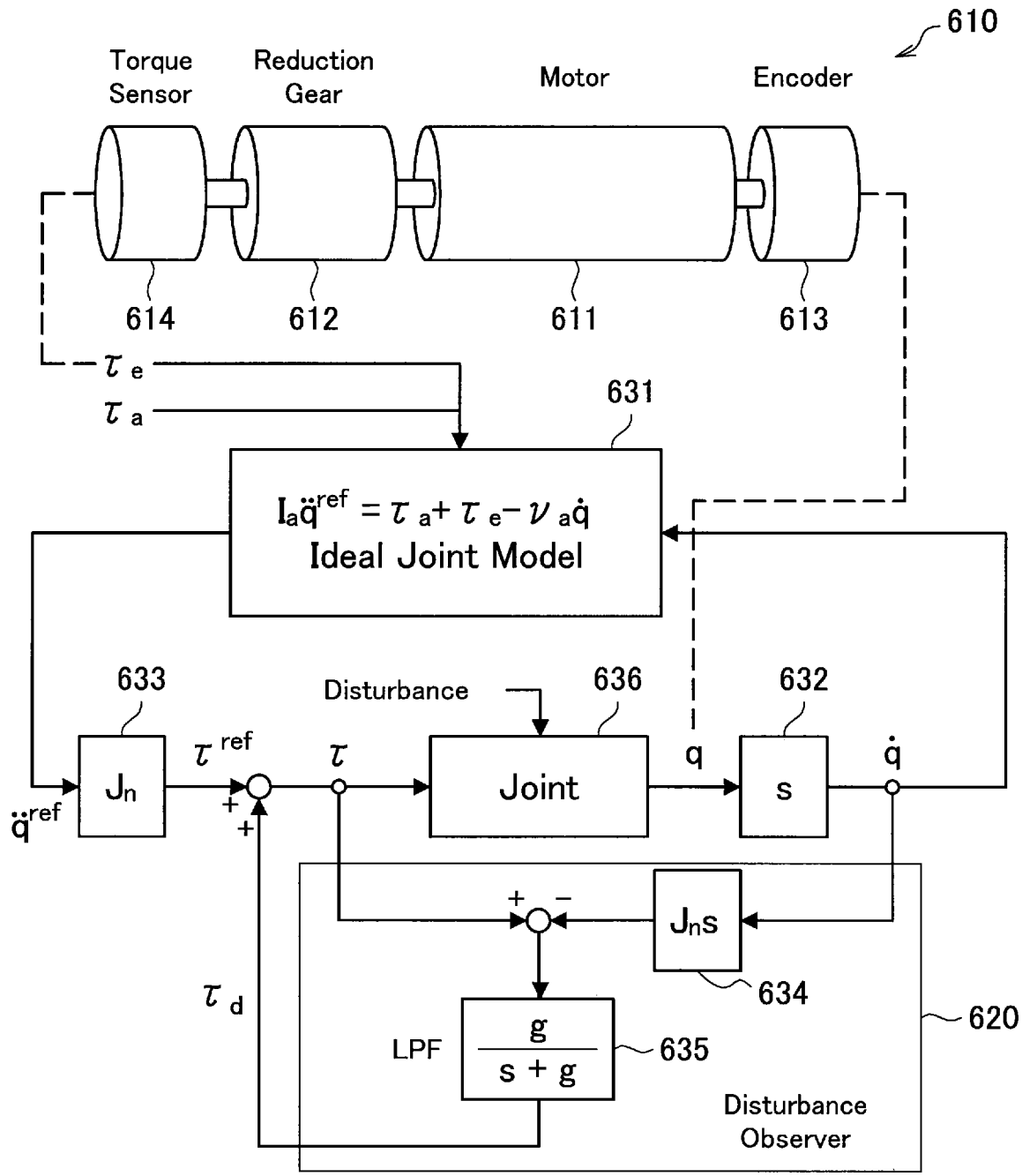

[Fig. 6]
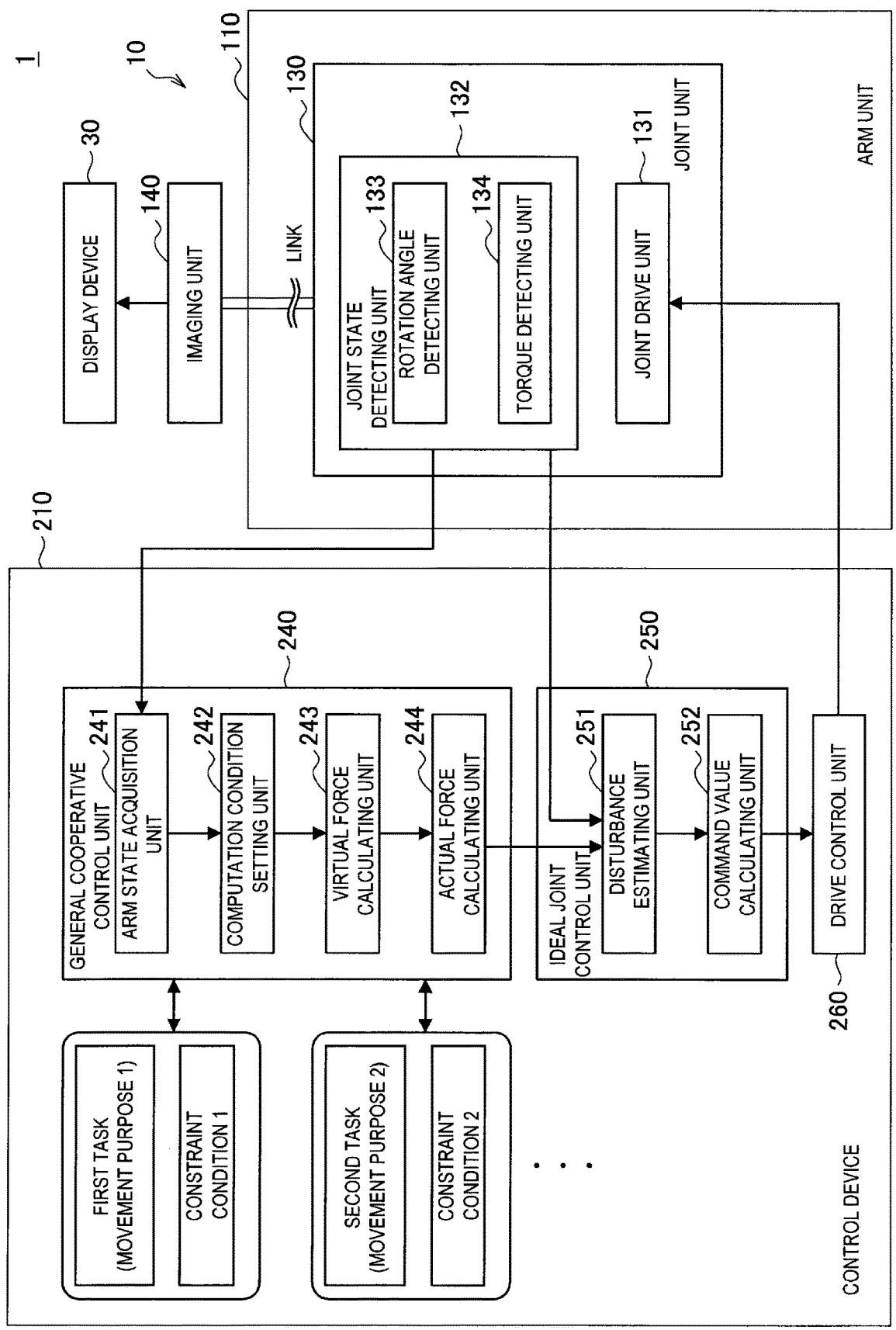

[Fig. 7]
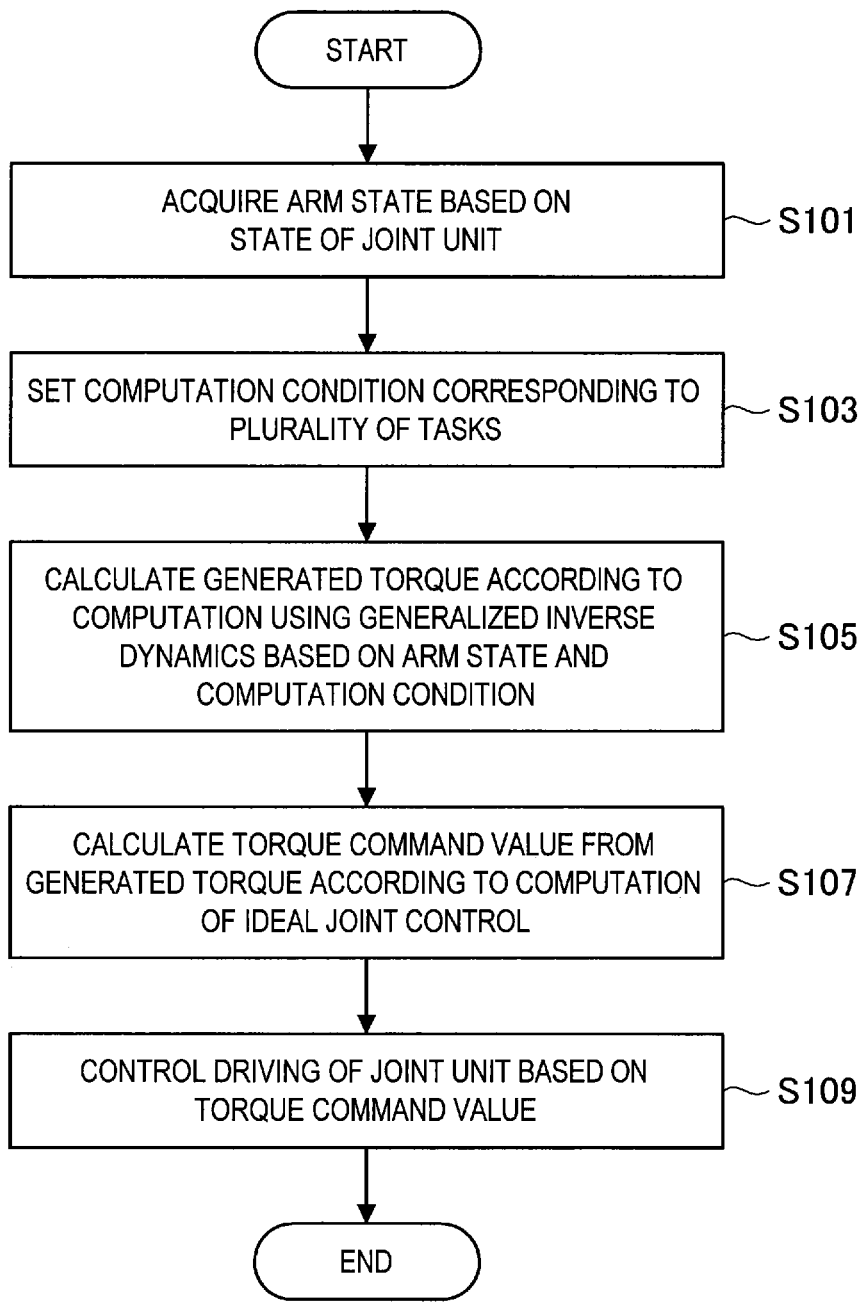

[Fig. 8]
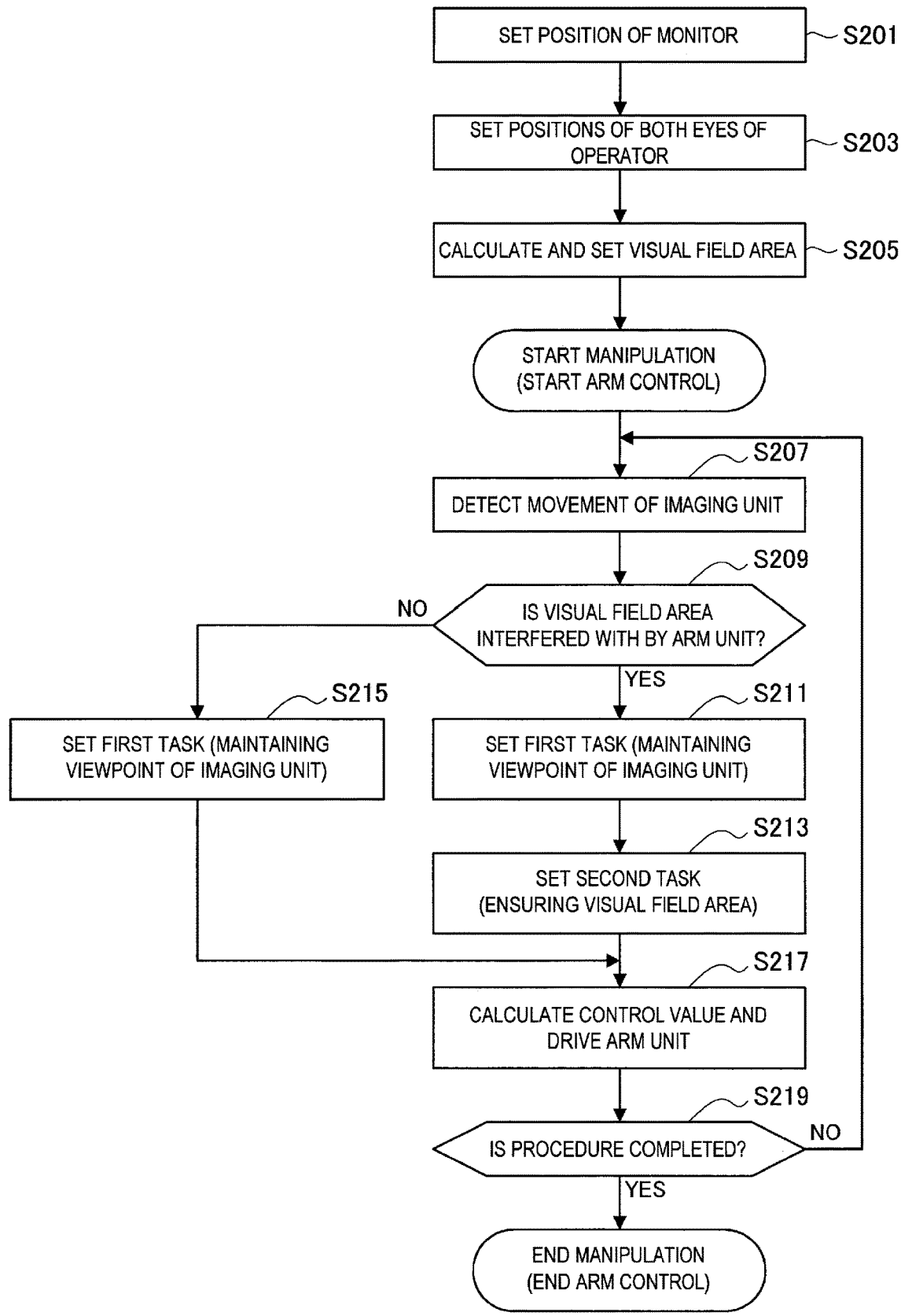

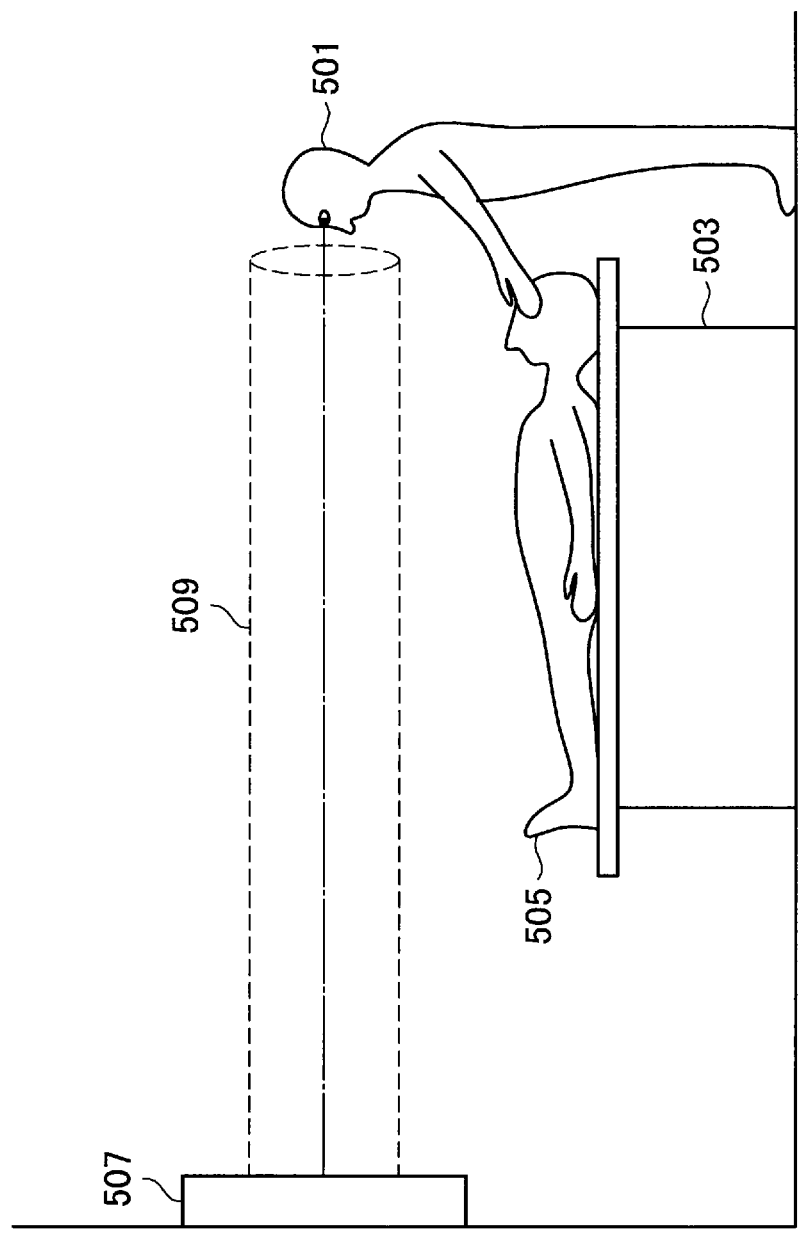
[Fig. 9]

[Fig. 10]
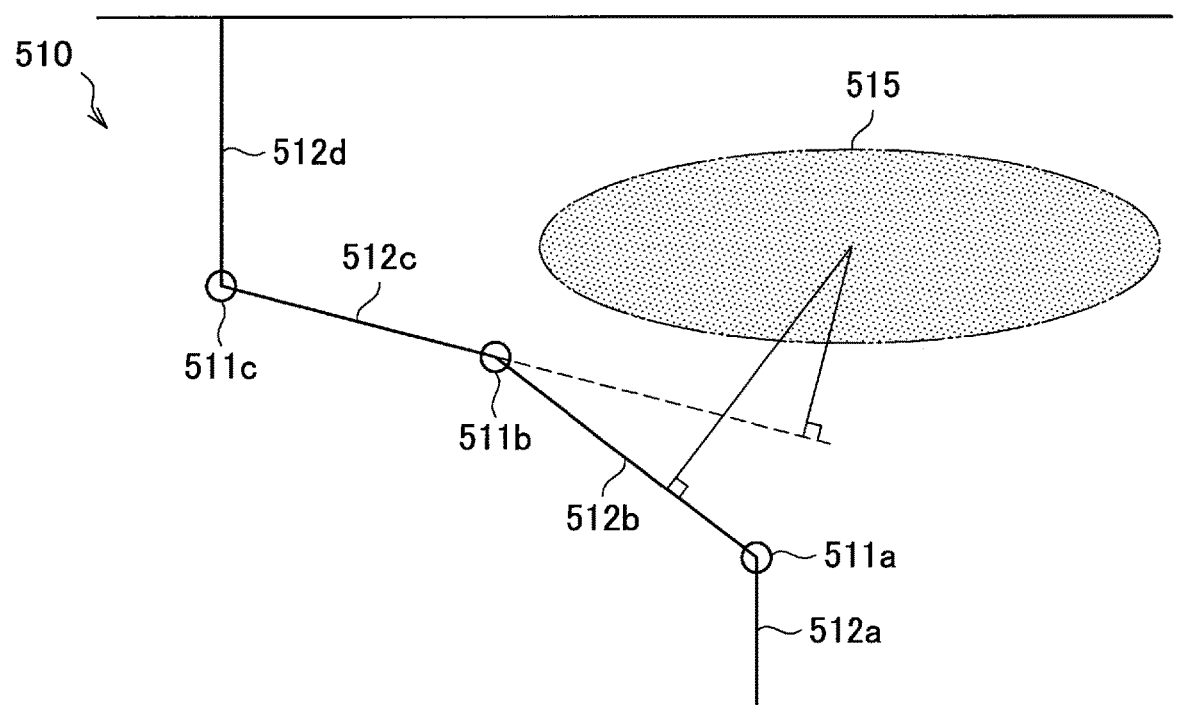

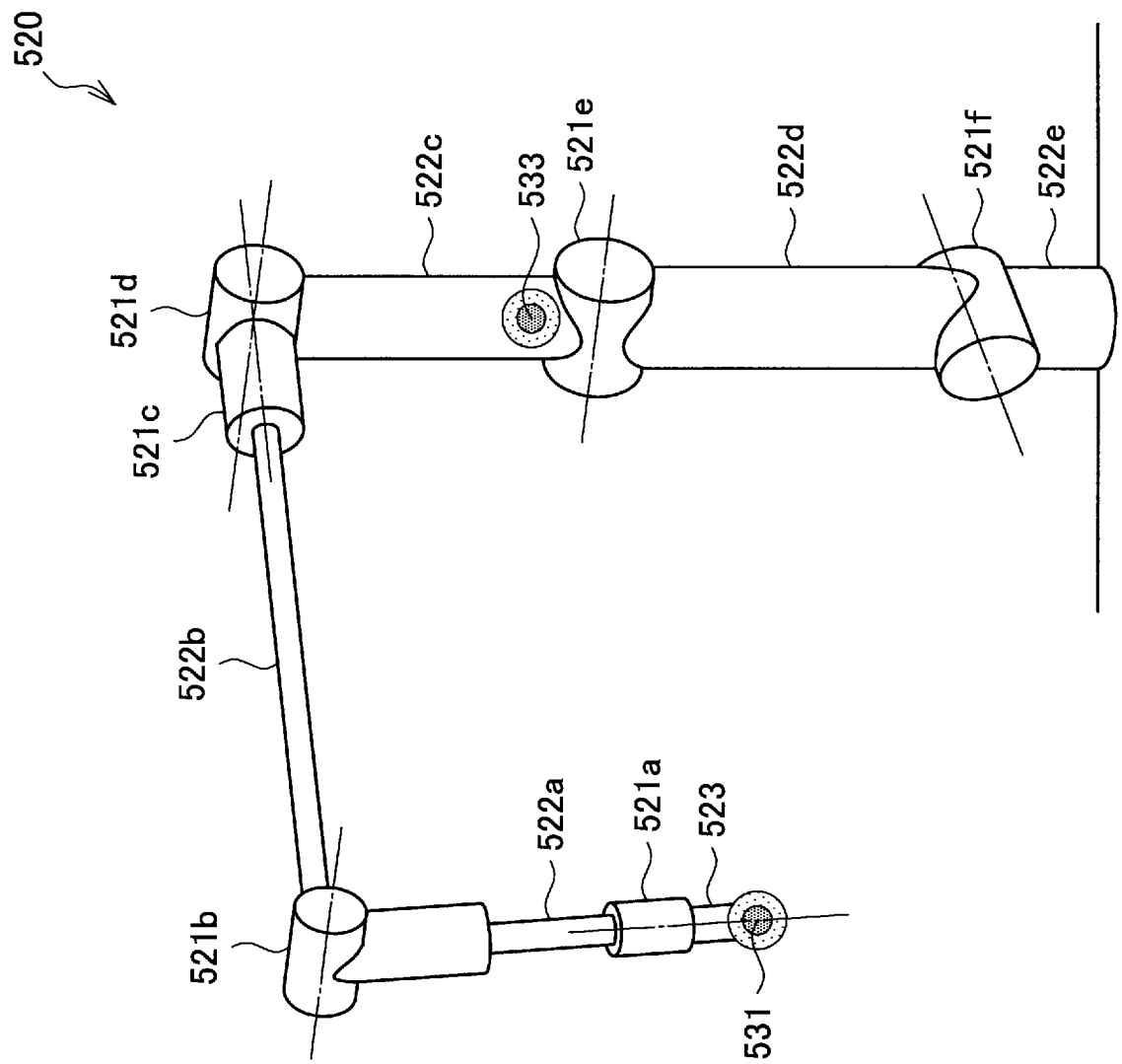
[Fig. 11]

[Fig. 12]
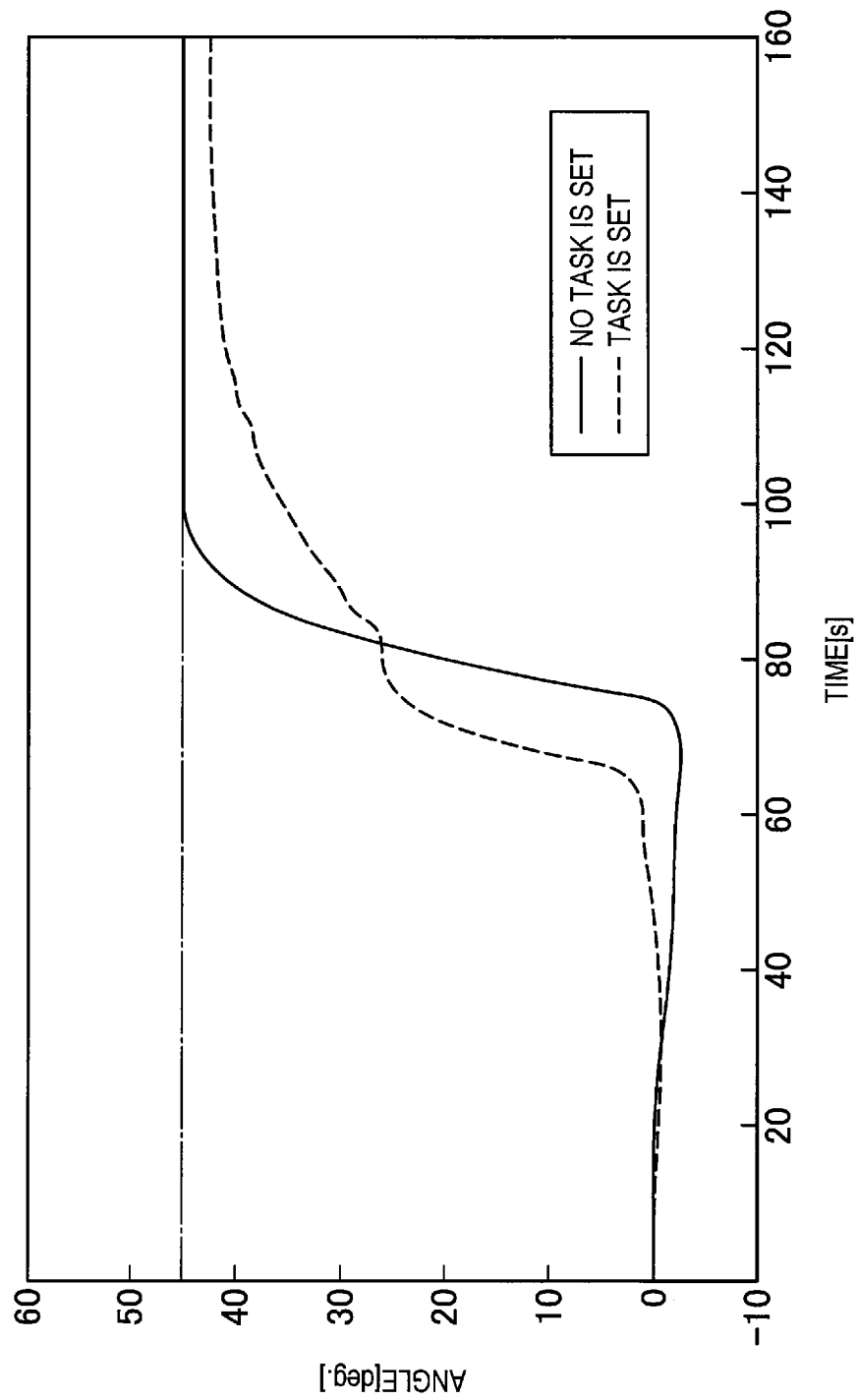

[Fig. 13]
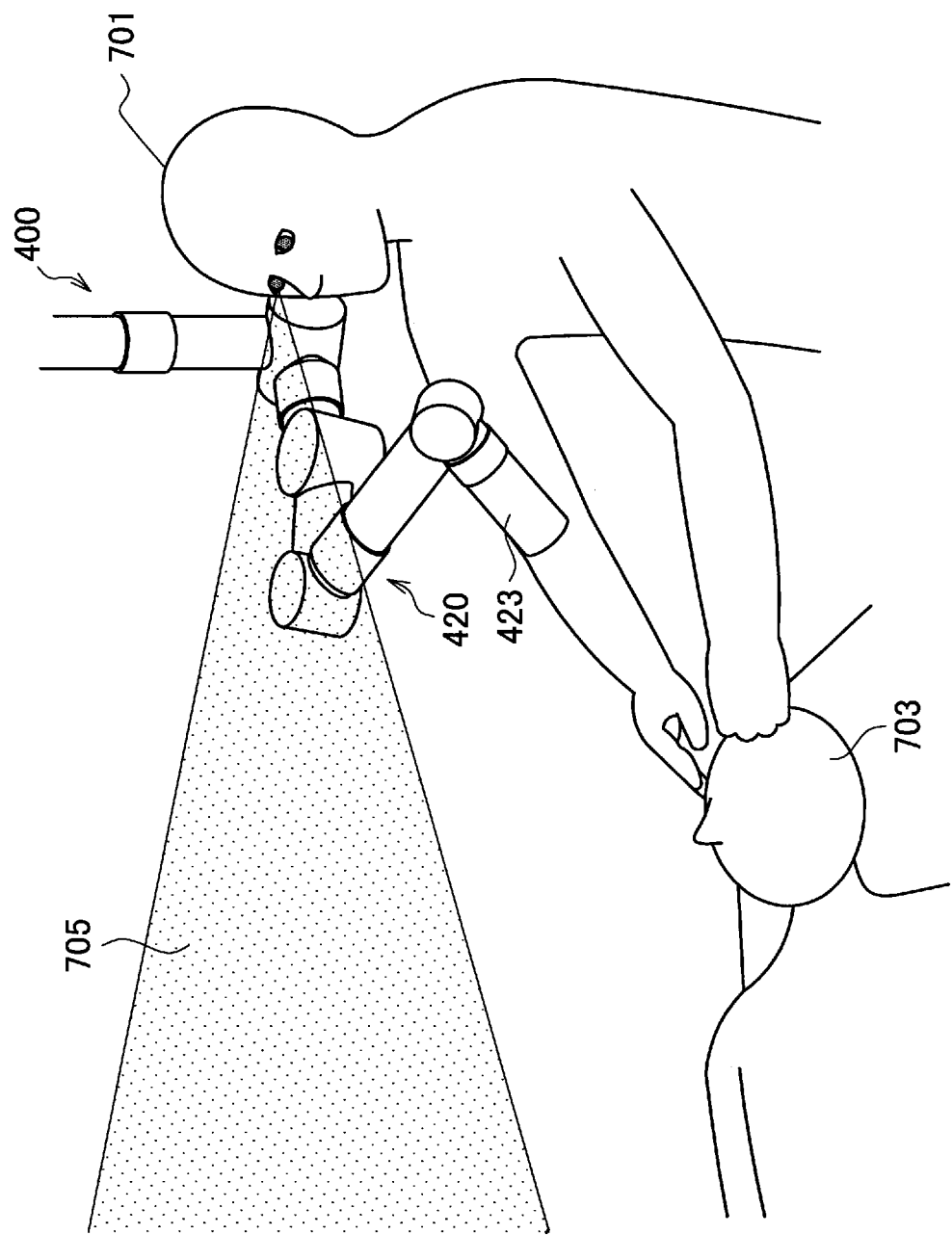

MEDICAL SUPPORT ARM DEVICE AND METHOD OF CONTROLLING MEDICAL SUPPORT ARM DEVICE

CROSS REFERENCE TO RELATED APPLICATIONS

This application claims the benefit of Japanese Priority Patent Application JP 2015-060166 filed Mar. 23, 2015, and Japanese Priority Patent Application JP 2015-208535 filed Oct. 23, 2015, the entire contents of each of which are incorporated herein by reference.

Technical Field

The present disclosure relates to a medical support arm device and a method of controlling a medical support arm device.

Background Art

In the field of medicine, support arm devices for supporting surgery have recently been used. For example, a method in which an observation unit that is used to observe an operation part such as a camera or an endoscope is provided at a leading end of an arm unit of a support arm device, and an operator performs surgery while viewing an image captured by the observation unit, has been proposed. Alternatively, a method in which a treatment instrument such as a forceps or a retractor is provided at a leading end of an arm unit, and supports or manipulations of the treatment instrument, which were performed by manpower in the related art, are performed by a support arm device, has been proposed.

In such support arm devices, while a medical instrument (for example, the above-described observation unit or treatment instrument) is supported by an arm unit including a plurality of joint units, technology in which the arm unit is configured to have a higher degree of freedom (that is, a redundant degree of freedom) than a degree of freedom necessary for implementing a predetermined movement purpose (task), and thus implementing a support arm device having higher convenience is proposed.

According to having a redundant degree of freedom, while a position and an orientation of a medical instrument attached at, for example, a leading end of an arm unit, are maintained, it is possible to change an orientation of the arm unit. Using such a technique, for example, Patent Literature 1 discloses technology in which, in a medical support arm device including a forceps arm for supporting a forceps and a camera arm for supporting an endoscope, both the forceps arm and the camera arm are configured to have a redundant degree of freedom, and when the forceps arm and the camera arm move and interfere with each other, driving of the camera arm and the forceps arm is controlled to avoid interference while a viewpoint of the endoscope is maintained.

CITATION LIST

Patent Literature

PTL 1: JP 2011-206312A
PTL 2: JP 2010-188471A

SUMMARY

Technical Problem

Here, in the technology disclosed in Patent Literature 1, control of a position and an orientation of a forceps and an endoscope is performed by a so-called position control. On the other hand, in general, a method called a force control is known as a method of controlling a so-called robot device having a plurality of driving shafts. In the position control, a command value of, for example, an angle, is assigned to an actuator of a joint unit, and driving of the actuator of each joint unit is controlled to follow the command value. On the other hand, in the force control, a target value of a force to be added to an operation target as a whole robot device is provided, and a generated torque of the actuator of each joint unit is controlled to implement the force indicated by the target value.

In general, in the position control, since it is difficult to flexibly respond to an external force, it is commonly referred to as a "hard control" and it is considered to be inappropriate for a robot device for performing tasks while performing physical interactions (for example, interpersonal physical interactions) with various outside objects. On the other hand, in the force control, since it is possible to implement a "soft control" at a power order, it is a particularly appropriate control method of a robot device configured to perform interpersonal physical interactions, and referred to as a control method having a higher usability.

For example, as a robot device to which the force control is applied, Patent Literature 2 discloses a robot device in which, in a robot device including a movement mechanism having two facing wheels and an arm portion having a plurality of joint units, driving of the wheels and the joint units is controlled as a whole in a cooperative manner.

When a control method using such a force control is applied to a medical support arm device having a redundant degree of freedom as described above, there is a possibility of implementing a support arm device having higher convenience. Therefore, the present disclosure proposes a medical support arm device, a method of controlling a medical support arm device, and a medical observation device which are novel and improved and through which it is possible to further increase user convenience.

Solution to Problem

According to an embodiment of the present disclosure, there is provided a medical support arm device including: a multi-joint arm having a distal end configured to host a medical device, said multi-joint arm configured to have a higher degree of freedom than a degree of freedom necessary for controlling a spatial position and pointing direction of the medical device. The multi-joint arm is configured to controllably displace at least one of a plurality of joints of the multi-joint arm while the spatial position and the pointing direction of the medical device are controlled.

According to an embodiment of the present disclosure, there is provided a medical support arm device including: a medical device configured to assist in a medical procedure on a patient; a multi-joint arm having a distal end to which the medical device is disposed configured to have a higher degree of freedom than a degree of freedom necessary for controlling a spatial position and a pointing direction of the medical device; and a drive controller configured to control a driving of a plurality of joint units of the multi-joint arm. In the multi-joint arm, when a spatial position and a pointing direction of the distal end of the multi-joint arm is controlled, the spatial position and the orientation of the medical device are controlled. The multi-joint arm is configured to change a pointing direction and a spatial position of the multi-joint arm when the spatial position and the pointing direction of the medical device are controlled.

According to an embodiment of the present disclosure, there is provided a method of controlling a medical support arm device including: controlling, by processing circuitry, driving of a multi-joint arm to that a spatial position and a pointing direction of the multi-joint arm is changeable when a spatial position and a pointing direction of a medical device are controlled when driving of a plurality of joints of the multi-joint arm are controlled. The movement of the multi-joint arm has a higher degree of freedom than a degree of freedom necessary for controlling the spatial position and the pointing direction of the medical device provided at a distal end of the multi-joint arm.

According to an embodiment of the present disclosure, since the multi-joint arm is configured to have a redundant degree of freedom, it is possible to simultaneously perform a plurality of tasks in the arm unit. Therefore, user convenience increases. In addition, since driving of the arm unit is controlled by a force control, the user can manipulate the arm unit more intuitively. Accordingly, user convenience further increases.

Advantageous Effects of Invention

According to an embodiment of the present disclosure described above, it is possible to further increase user convenience. Also, the above effects are not necessarily limited, and any effect shown in this specification or other effects that may be understood from this specification may be accomplished along with these effects or instead of these effects.

BRIEF DESCRIPTION OF DRAWINGS

FIG. 1 is a diagram illustrating an overall configuration of a support arm device according to the present embodiment.

FIG. 2 is a cross sectional view of an exemplary configuration of an actuator mounted on a joint unit of the support arm device illustrated in FIG. 1.

FIG. 3 is a diagram illustrating an exemplary operation of an arm unit when 7 degrees of freedom are implemented in the arm unit illustrated in FIG. 1.

FIG. 4 is a diagram illustrating an exemplary operation of an arm unit when 8 degrees of freedom are implemented in the arm unit illustrated in FIG. 1.

FIG. 5 is a diagram for describing an ideal joint control according to the present embodiment.

FIG. 6 is a functional block diagram illustrating an exemplary functional configuration of the support arm device according to the present embodiment.

FIG. 7 is a flowchart showing an exemplary processing procedure of a method of controlling a support arm device according to the present embodiment.

FIG. 8 is a flowchart showing an exemplary processing procedure of the method of controlling a support arm device according to the present embodiment when "ensuring a visual field area" is set as a task.

FIG. 9 is a diagram for describing a process of setting a visual field area.

FIG. 10 is a diagram for describing a distance between a visual field area and an arm unit.

FIG. 11 is a diagram illustrating a configuration of an arm unit used in an experiment of drive control when "avoiding a mechanically limited orientation" is set as a task.

FIG. 12 shows the graph of results of drive control of an arm unit when "avoiding a mechanically limited orientation" is set as a task.

FIG. 13 is a diagram schematically illustrating a state in which surgery is performed using a support arm device according to the present embodiment.

DESCRIPTION OF EMBODIMENTS

Exemplary embodiments of the present disclosure will be described in detail below with reference to the accompanying drawings. In the specification and drawings, components that have substantially the same functional configuration are denoted with the same reference numerals, and repeated descriptions thereof will be omitted.

Hereinafter, the description will proceed in the following order

1. Configuration of Support Arm Device
1-1. Overall Configuration of Support Arm Device
1-2. Configuration of Actuator
1-3. Degree of Freedom of Support Arm Device
2. Functional Configuration of Support Arm Device
2-1. Overview of Control
2-1-1. About Generalized Inverse Dynamics
2-1-1-1. Virtual Force Calculating Process
2-1-1-2. Actual Force Calculating Process
2-1-2. About Ideal Joint Control
2-2. Functional Configuration
3. Specific Example of Tasks
3-1. Maintaining Viewpoint of Imaging Unit
3-2. Pivot Operation
3-3. Ensuring Visual Field Area
3-4. Avoiding Specific Orientation
3-5. Avoiding Mechanically limited Orientation
3-6. Energy Minimization
4. Method of Controlling Support Arm Device
5. Specific Example of Control Method
5-1. When "ensuring a visual field area" is set as a task
5-2. When "avoiding a mechanically limited orientation" is set as a task
6. Application Example
7. Supplement Note that, hereinafter, a user who performs various manipulations on an observation system and/or a support arm device according to one embodiment of the present disclosure will be described as an operator for convenience of description. However, the description is not intended to limit the user who uses the observation system and/or the support arm device, and various manipulations on the observation system and/or the support arm device may also be performed by any user such as other medical staff.

(1. Configuration of Support Arm Device)
(1-1. Overall Configuration of Support Arm Device)

As illustrated in FIG. 1, an overall configuration of a support arm device according to one embodiment of the present disclosure will be described. FIG. 1 is a diagram illustrating an overall configuration of a support arm device according to the present embodiment.

As illustrated in FIG. 1, a support arm device 400 according to the present embodiment includes an arm unit (or multi-joint arm) 420, an imaging unit 423 attached at a leading (distal) end of the arm unit 420, and a control device (controller or circuitry) 440 configured to control an operation of the support arm device 400. The support arm device 400 is a medical support arm device 400 that is provided in an operating room and supports an operator (a user) to perform surgery.

The arm unit 420 has a base end portion attached to a ceiling of the operating room and is installed to be suspended from the ceiling. While the control device 440 is schematically illustrated in FIG. 1, the control device 440 may be actually provided at a portion connecting the base end portion of the arm unit 420 and the ceiling, or may be installed at a position (for example, on the floor of the operating room) separated from the arm unit 420, and provided to be communicatively connected to the arm unit 420 through various wired or wireless communication methods.

Also, in the following description, when a configuration of the arm unit 420 is described, a side at which the imaging unit 423 is provided is referred to as a leading end side or a leading end portion, and a side close to the ceiling is referred to as a base end side or a base end portion.

The arm unit 420 includes joint units 421a, 421b, 421c, 421d, 421e, 421f, 421g, and 421h provided at positions corresponding to axes of rotation (a first axis $O_1$, a second axis $O_2$, a third axis $O_3$, a fourth axis $O_4$, a fifth axis $O_5$, a sixth axis $O_6$, a seventh axis $O_7$, and an eighth axis $O_8$), respectively, and a plurality of links 422a, 422b, 422c, 422d, 422e, 422f, 422g, and 422h that are rotatably linked to each other by the joint units 421b to 421g. In addition, the imaging unit 423 is rotatably attached at the leading end of the arm unit 420 through the joint unit 421a.

The links 422a to 422g are cylindrical members, and a base end of the link 422h is attached to the ceiling. A leading end of the link 422h is linked to a base end of the link 422g through the joint unit 421h. The link 422h rotatably supports the link 422g through the joint unit 421h.

Hereinafter, similarly, leading ends of the links 422g, 422f, 422e, 422d, 422c, and 422b are linked to base ends of the links 422f, 422e, 422d, 422c, 422b, and 422a through the joint units 421g, 421f, 421e, 421d, 421c, and 421b, respectively. Therefore, the links 422g, 422f, 422e, 422d, 422c, and 422b rotatably support the links 422f, 422e, 422d, 422c, 422b, and 422a through the joint units 421g, 421f, 421e, 421d, 421c, and 421b, respectively.

The imaging unit 423 is linked to a leading end of the link 422a through the joint unit 421a. The link 422a rotatably supports the imaging unit 423 through the joint unit 421a.

In this manner, using the base end of the link 422h connected to the ceiling as a fulcrum, ends of the plurality of links 422a to 422h are linked to each other by the joint units 421b to 421h, and thus configure an arm shape extending from the ceiling.

Among the axes of rotation, the first axis $O_1$, the third axis $O_3$, the sixth axis $O_6$, and the eighth axis $O_8$ are axes of rotation in a direction substantially parallel to an extending direction of the links 422a, 422c, 422f, and 422h provided at a base end side thereof. The axis of rotation having such a direction is also referred to as a yaw axis in this specification for convenience of description. On the other hand, the second axis $O_2$, the fourth axis $O_4$, the fifth axis $O_5$, and the seventh axis $O_7$ are axes of rotation in a direction substantially orthogonal to an extending direction of the links 422b, 422d, 422e, and 422g provided at a base end side thereof. The axis of rotation having such a direction is also referred to as a pitch axis in this specification, for convenience of description.

That is, the arm unit 420 is configured in a manner that the yaw axis (the eighth axis $O_8$), the pitch axis (the seventh axis $O_7$), the yaw axis (the sixth axis $O_6$), the pitch axis (the fifth axis $O_5$), the pitch axis (the fourth axis $O_4$), the yaw axis (the third axis $O_3$), the pitch axis (the second axis $O_2$), and the yaw axis (the first axis $O_1$) are sequentially disposed from the base end side.

An actuator 430 (to be described below) illustrated in FIG. 2 is provided at the joint units 421a to 421h. The joint units 421a to 421h are driven by the actuators 430 to rotate about a predetermined axis of rotation. Driving of the actuator 430 is controlled by the control device 440. When driving of the actuator 430 of each of the joint units 421a to 421h is controlled, driving of the arm unit 420 is controlled, for example, the arm unit 420 is extended, or shortened (folded).

The imaging unit 423 is an exemplary observation unit that is used to observe an operation part, and is configured as, for example, observation optics including imaging circuitry, a camera capable of imaging a video and/or a still image of an imaging target. The imaging unit 423 may be a so-called video microscope.

When surgery is performed, spatial positions and orientations (deployment configurations) of the arm unit 420 and the imaging unit 423 are controlled in a manner that the imaging unit 423 provided at the leading end of the arm unit 420 images a patient's operation part from the outside of a body so that the imaging unit 423 is oriented in a pointing direction toward the operation site on/in the patient's body. An image signal of the operation part captured by the imaging unit 423 is transmitted to, for example, a display device (not illustrated) provided in the operating room. An image of the patient's operation part is displayed on the display device based on the transmitted image signal. The operator performs surgery while observing the operation part through the image projected on the display device. Also, communication between the imaging unit 423 and the display device may be implemented by various known wired or wireless communication methods. In addition, since configurations of various known video microscopes may be applied as a specific configuration of the imaging unit 423, detailed descriptions thereof will be omitted herein.

Here, as the support arm device 400, the support arm device 400 in which the observation unit that is used to observe the patient's operation part is provided at the leading end of the arm unit 420 is provided, and is also referred to as an observation device 400 in the present embodiment. In the illustrated example, the imaging unit 423 is provided as the observation unit, and the present embodiment is not limited thereto. As the observation unit, for example, an endoscope or an optical microscope (or other medical tool) may be provided. Also, in the present embodiment, among the observation devices 400, in particular, the support arm device 400 in which the imaging unit 423 of the video microscope is provided at the leading end of the arm unit 420 is also referred to as a video microscope device 400.

However, in the present embodiment, the unit provided at the leading end of the arm unit 420 is not limited to the observation unit, and various medical instruments may be attached at the leading end of the arm unit 420. For example, various treatment instruments such as a forceps and a retractor may be connected to the leading end of the arm unit 420. Alternatively, a light source for an endoscope or a microscope, or a surgical energy device used for, for example, blood vessel suturing, may be connected to the leading end of the arm unit 420.

Also, while the configuration example illustrated in FIG. 1 shows that the imaging unit 423 is directly attached at the leading end of the arm unit 420, the present embodiment is not limited thereto. For example, a holding unit configured to hold various medical instruments including the imaging unit 423 may be attached at the leading end of the arm unit 420, and various medical instruments may be supported by the arm unit 420 through the holding unit. In this case, when a position and an orientation of the holding unit are controlled, a position and an orientation of the medical instrument may be controlled. That is, when a movement purpose (task) to be described below is set for an operation of the medical instrument, the task may be set for an operation of the holding unit. For example, when the endoscope is attached at the leading end of the arm unit 420 in the observation unit, the endoscope may be appropriately attached at the leading end of the arm unit 420 through the holding unit.

The control device 440 includes, for example, a processor such as a central processing unit (CPU) and a digital signal processor (DSP), or a microcomputer on which such a processor is mounted, and controls an operation of the support arm device 400 when signal processing is performed according to a predetermined program.

In the present embodiment, as a method of controlling the support arm device 400, a force control is appropriately used. In the force control, a force applied to the arm unit 420 and the imaging unit 423 is detected by a torque sensor of the actuator 430 provided at each of the joint units 421a to 421h. Based on the detected force, a torque that is necessary for the arm unit 420 to accomplish a desired movement purpose (task) and generated by the actuator 430 provided at each of the joint units 421a to 421h is calculated. Driving of the arm unit 420 is controlled using the calculated generated torque as a control value.

In the force control, driving of each of the joint units 421a to 421h is controlled according to an external force against the arm unit 420. Specifically, in the force control, driving of the actuator 430 is controlled by the control device 440 in a manner that the arm unit 420 is moved (that is, so as to follow an operation of the operator) in a direction of a force applied to the arm unit 420 according to, for example, a manipulation of the operator directly touching the arm unit 420 and moving the arm unit 420, and an operation of the arm unit 420 may be controlled. In this manner, when the force control is used, since the operator can move the arm unit 420 while directly touching the arm unit 420, it is possible to perform a manipulation easily and more intuitively. Also, in the following description, a manipulation of the operator moving the arm unit 420 while directly touching the arm unit 420 is referred to as a direct manipulation.

Here, in the present embodiment, the arm unit 420 has 8 axes of rotation, and is configured to have 8 degrees of freedom for driving of the arm unit 420. In order for the imaging unit 423 to have any position and orientation, a movement of a total of six degrees of freedom including 3 translational degrees of freedom and 3 rotational degrees of freedom in the imaging unit 423 should be implemented. Therefore, the arm unit 420 has a redundant degree of freedom through which it is possible to perform an operation freely even when a position and an orientation of the imaging unit 423 are uniquely defined.

In the present embodiment, in this manner, the arm unit 420 is configured to have a redundant degree of freedom. Then, the control device 440 controls driving of the arm unit 420 in a manner that the arm unit 420 simultaneously performs a plurality of tasks using the redundant degree of freedom. Therefore, the support arm device 400 having higher user convenience may be implemented.

Note that, a degree of freedom of the arm unit 420 will be described again in detail in the following (1-3. Degree of Freedom of Support Arm Device). In addition, a specific method of controlling the support arm device 400 will be described again in detail in the following (4. Method of Controlling Support Arm Device).

(1-2. Configuration of Actuator)

A configuration of an actuator mounted on each of the joint units 421a to 421h of the support arm device 400 illustrated in FIG. 1 will be described with reference to FIG. 2. FIG. 2 is a cross sectional view of an exemplary configuration of an actuator mounted on the joint units 421a to 421h of the support arm device 400 illustrated in FIG. 1. FIG. 2 is a cross sectional view of an actuator according to the present embodiment taken along a plane passing through an axis of rotation.

As illustrated in FIG. 2, the actuator 430 according to the present embodiment includes a motor 424, a motor driver 425, a decelerator 426, an encoder 427, and a torque sensor 428. The actuator 430 is an actuator corresponding to, for example, the force control. In the actuator 430, rotation of the motor 424 is decelerated at a predetermined reduction ratio by the decelerator 426, and delivered to other members in subsequent stages through an output shaft, and thereby the other members are driven.

The motor 424 is a drive mechanism in which, when a predetermined command value (a current command value) is assigned, a rotary shaft is rotated at a rotational speed corresponding to the command value, and thereby a driving force is generated. As the motor 424, for example, a brushless motor is used. However, the present embodiment is not limited thereto, and various known motors may be used as the motor 424.

The motor driver 425 is a driver circuit (a driver integrated circuit (IC)) that drives the motor 424 to rotate when a current is supplied to the motor 424, and can control the number of rotations of the motor 424 when an amount of current supplied to the motor 424 is regulated. When a current corresponding to a torque command value τ illustrated in FIG. 5 to be described below is supplied to the motor 424, the motor driver 425 drives the motor 424.

In addition, when an amount of current supplied to the motor 424 is regulated, the motor driver 425 can regulate a viscosity resistance coefficient in a rotating operation of the actuator 430. Accordingly, it is possible to load a predetermined resistance on the rotating operation in the actuator 430, that is, a rotating operation in the joint units 421a to 421h. For example, the joint units 421a to 421h can be in a state in which rotation is easily performed according to a force applied from the outside (that is, in a state in which the arm unit 420 is manually moved with ease), on the other hand, the join units 421a to 421h can be in a state in which rotation is not easily performed according to a force applied from the outside (that is, in a state in which it is difficult to manually move the arm unit 420).

The decelerator 426 is linked to a rotary shaft (a driving shaft) of the motor 424. The decelerator 426 decelerates a rotational speed (that is, a rotational speed of an input shaft) of the linked rotary shaft of the motor 424 at a predetermined reduction ratio and delivers the result to an output shaft. In the present embodiment, a configuration of the decelerator 426 is not specifically limited, and various known decelerators may be used as the decelerator 426. However, as the decelerator 426, a decelerator capable of setting a reduction ratio with high accuracy, for example, a harmonic drive (registered trademark), is preferably used. In addition, a reduction ratio of the decelerator 426 may be appropriately set according to an application of the actuator 430. For example, in the present embodiment, as long as the actuator 430 is applied to the joint units 421a to 421h of the support arm device 400, the decelerator 426 having a reduction ratio of about 1:100 may be appropriately used.

The encoder 427 detects a rotation angle (that is, a rotation angle of the rotary shaft of the motor 424) of the input shaft. Information on a rotation angle, a rotation angular velocity, a rotation angular acceleration, and the like of the joint units 421a to 421h can be obtained based on the number of rotations of the input shaft detected by the encoder 427 and the reduction ratio of the decelerator 426. As the encoder 427, various known rotary encoders, for example, a magnetic encoder and an optical encoder, may be used. Also, in the illustrated example, while the encoder 427 is provided at only the input shaft of the actuator 430, an encoder for detecting a rotation angle of the output shaft of the actuator 430 or the like may be further provided in a stage subsequent to the decelerator 426.

The torque sensor 428 is connected to the output shaft of the actuator 430 and detects a torque applied to the actuator 430. The torque sensor 428 detects a torque (a generated torque) output by the actuator 430. The torque sensor 428 can also detect an external torque applied to the actuator 430 from the outside.

The configuration of the actuator 430 according to the present embodiment has been described above with reference to FIG. 2. When the force control is performed, in the support arm device 400, a rotation angle of each of the joint units 421a to 421h, and a torque applied to each of the joint units 421a to 421h are detected by the encoder 427 and the torque sensor 428 provided in each of the actuators 430. In this case, the torque applied to each of the joint units 421a to 421h detected by the torque sensor 428 may include a force applied to the arm unit 420 and/or the imaging unit 423.

Based on the rotation angle detected by the encoder 427 and the torque value detected by the torque sensor 428, a state of the arm unit 420 (for example, a position and a speed) may be obtained. In the support arm device 400, a torque that is necessary for the arm unit 420 to perform a desired task and generated by the actuator 430 of each of the joint units 421a to 421h is calculated based on the obtained state of the arm unit 420 (a state of the arm), and the actuator 430 of each of the joint units 421a to 421h is driven using the torque as a control value.

Also, the configuration illustrated in FIG. 2 is only an exemplary configuration of the actuator 430 according to the present embodiment, and the present embodiment is not limited thereto. As the actuator 430, various known actuators used in various devices whose operation is generally controlled by the force control can be used.

(1-3. Degree of Freedom of Support Arm Device)

As described with reference to FIG. 1, in the present embodiment, the arm unit 420 is configured to have 8 degrees of freedom. In order for the imaging unit 423 provided at the leading end of the arm unit 420 to have any position and orientation, a movement of a total of 6 degrees of freedom in the imaging unit 423 should be implemented. Therefore, the arm unit 420 may be understood to have a redundant degree of freedom through which an orientation thereof can be changed even when the position and the orientation of the imaging unit 423 are uniquely defined. In other words, the arm unit 420 is configured in a manner that an orientation of the arm unit 420 can be changed when the position and the orientation of the imaging unit 423 are controlled.

Here, if the support arm device 400 has only a minimum degree of freedom (that is, 6 degrees of freedom) for arbitrarily defining the position and the orientation of the imaging unit 423, when the position and the orientation of the imaging unit 423 are uniquely determined, the orientation of the arm unit 420 is also uniquely determined. For example, in the configuration of the arm unit 420 illustrated in FIG. 1, a case in which rotation in the joint units 421e and 421f (the fifth axis $O_5$ and the sixth axis $O_6$) is fixed is considered. In this case, the arm unit 420 can be considered as having 6 degrees of freedom. In this state, when the position and the orientation of the imaging unit 423 are uniquely determined, the orientation of the arm unit 420 is also determined as a predetermined orientation (for example, an orientation illustrated in FIG. 1), and other orientations may not be obtained.

Next, for example, in the configuration of the arm unit 420 illustrated in FIG. 1, a case in which rotation in the joint unit 421e (the fifth axis $O_5$) is fixed is considered. In this case, the arm unit 420 has 7 degrees of freedom, that is, the arm unit 420 can be considered as having one redundant degree of freedom in addition to degrees of freedom necessary for performing a task of maintaining the position and the orientation of the imaging unit 423. FIG. 3 is a diagram illustrating an exemplary operation of the arm unit 420 when such 7 degrees of freedom are implemented in the arm unit 420 illustrated in FIG. 1.

As illustrated in FIG. 3, if 7 degrees of freedom are provided, even when the position and the orientation of the imaging unit 423 are uniquely determined, a configuration from the joint unit 421b of the arm unit 420 to the joint unit 421g can be moved to rotate using a linear line passing through the joint unit 421b and the joint unit 421g as an axis of rotation while the position and the orientation of the imaging unit 423 are maintained.

Furthermore, for example, in the configuration of the arm unit 420 illustrated in FIG. 1, a case in which all of the joint units 421a to 421h are rotatable is considered. In this case, the arm unit 420 has 8 degrees of freedom, that is, the arm unit 420 can be considered as having two redundant degrees of freedom in addition to degrees of freedom necessary for performing the task of maintaining the position and the orientation of the imaging unit 423. FIG. 4 is a diagram illustrating an exemplary operation of the arm unit 420 when such 8 degrees of freedom are implemented in the arm unit 420 illustrated in FIG. 1.

As illustrated in FIG. 4, when 8 degrees of freedom are provided, similarly to the case having 7 degrees of freedom, a configuration from the joint unit 421b of the arm unit 420 to the joint unit 421g can be moved to rotate using the linear line passing through the joint unit 421b and the joint unit 421g as an axis of rotation while the position and the orientation of the imaging unit 423 are maintained. In addition, when 8 degrees of freedom are provided, in addition thereto, according to rotation in the joint unit 421d (rotation about the fifth axis $O_5$), a configuration from the joint unit 421b of the arm unit 420 to the joint unit 421g can be moved to be folded in an extending direction thereof.

In this manner, when the arm unit 420 is configured to have a redundant degree of freedom, in the support arm device 400, while a task (in the above example, the task of maintaining the position and the orientation of the imaging unit 423) is performed, the orientation of the arm unit 420 is changed, and other tasks can be performed. Also, in the following description, in order to distinguish a plurality of tasks performed in the support arm device 400, these tasks are denoted by numbers for convenience of description and referred to as a first task, a second task, or the like.

Also, in the above example, since the task of maintaining the position and the orientation of the imaging unit 423 is set as the first task and 6 degrees of freedom are necessary to perform the task, the arm unit 420 having 7 degrees of freedom or 8 degrees of freedom has been described as the arm unit 420 having a redundant degree of freedom. However, this is only an example. In order for the arm unit 420 to have a redundant degree of freedom, the arm unit 420 may have a higher degree of freedom than a degree of freedom necessary for performing the first task. For example, when a degree of freedom necessary for performing the first task is 5 degrees of freedom, the arm unit 420 having 6 or more degrees of freedom can be considered as the arm unit 420 having a redundant degree of freedom.

Here, in general, a movement of an arm structure having a configuration in which a plurality of links are linked to each other by joint units may be represented by the following Expression (1). Here, x denotes a vector of coordinates indicating positions of leading ends of the links of the arm structure, and θ denotes a vector of rotation angles in the joint units (rotation angles of other links with respect to one of the links linked by the joint unit). In addition, J(θ) denotes a Jacobian matrix (Jacobian) of x for θ.

[Math.1]

$$\dot{x}(\theta) = J(\theta)\dot{\theta} \qquad (1)$$

In addition, a solution satisfying Expression (1) is known to be generally represented by the following Expression (2). Also, J+(θ) denotes a pseudo inverse matrix of J(θ).

[Math.2]

$$\dot{\theta} = J^+(\theta)r(t) + (I - J^+(\theta)J(\theta))v(t) \qquad (2)$$

Here, r(t) denotes a first task, and v(t) denotes a second task. That is, a coefficient $(I-J^+(\theta)J(\theta))$ of v(t) in the second term on the right-hand side of Expression (2) may denote a remaining redundancy when the first task r(t) is performed.

Expression (2) indicates the fact that a plurality of tasks can be simultaneously performed in the arm unit 420 having a redundant degree of freedom. Using this fact, in the present embodiment, driving of the arm unit 420 is controlled in a manner that the plurality of tasks are simultaneously performed.

For example, as described in the above (1-1. Overall Configuration of Support Arm Device), in surgery using the support arm device 400, the position and the orientation of the imaging unit 423 are maintained by the support arm device 400, and an image captured by the imaging unit 423 is displayed on the display device in the operating room. Then, the operator performs the surgery while referring to the image of the operation part displayed on the display device. In this case, since the imaging unit 423 and the arm unit 420 supporting the imaging unit 423 may be positioned between the operator and the display device, a field of view of the operator who observes the display device may be blocked by the arm unit 420. When the field of view of the operator is blocked, since there is a possibility of a smooth progress of the surgery being interrupted, such a situation is not preferable.

On the other hand, as described above, the support arm device 400 according to the present embodiment can change the orientation of the arm unit 420 while the position and the orientation of the imaging unit 423 are maintained. For example, as illustrated in FIG. 3, when a configuration from the joint unit 421b of the arm unit 420 to the joint unit 421g is rotated using the linear line passing through the joint unit 421b and the joint unit 421g as an axis of rotation, the configuration can be moved away from the field of view of the operator. Similarly, for example, as illustrated in FIG. 4, when a configuration from the joint unit 421b of the arm unit 420 to the joint unit 421g is rotated using the linear line passing through the joint unit 421b and the joint unit 421g as an axis of rotation and the configuration is operated to be folded in an extending direction thereof, the configuration can be further moved away from the field of view of the operator.

In this manner, when the support arm device 400 according to the present embodiment has a redundant degree of freedom, the task of maintaining the position and the orientation of the imaging unit 423 (that is, a task of maintaining a viewpoint of the imaging unit 423) and another task of ensuring a visual field area of the operator can be simultaneously performed. In this manner, according to the present embodiment, when the plurality of tasks are simultaneously performed, it is possible to further increase user convenience.

Furthermore, in the support arm device 400 according to the present embodiment, driving of the arm unit 420 may be appropriately controlled by the force control. Therefore, since the operator can perform a manipulation more intuitively, the support arm device 400 having higher operability may be implemented when a plurality of desired tasks are performed.

Also, the above-described task is an example among tasks that may be performed by the arm unit 420 of the support arm device 400 according to the present embodiment. The arm unit 420 may also perform other tasks. In addition, the number of tasks that are simultaneously performed by the arm unit 420 is not limited to 2, but the arm unit 420 may simultaneously perform more tasks. Also, a specific exemplary task that may be performed by the arm unit 420 according to the present embodiment will be described in detail in the following (3. Specific Example of Tasks).

In addition, a configuration of the arm unit 420 is not limited to the illustration in FIG. 1. The configuration of the arm unit 420 (for example, the number of joint units, a direction of an axis of rotation in the joint unit, a position in which the joint unit is disposed, the number of links, a length of the link, and the like) may be appropriately set according to a type of the task performed by the arm unit 420. Therefore, a movable range and an orientation necessary for the arm unit 420 may be determined according to a type of the task. In other words, the configuration of the arm unit 420 may be appropriately set in a manner that a movable range and an orientation necessary for the arm unit 420 determined according to the task may be implemented.

For example, in the configuration illustrated in FIG. 1, in the arm unit 420, there is a portion (the joint units 421e and 421f (the fifth axis $O_5$ and the sixth axis $O_6$)) in which the pitch axis is continuous. However, in the arm unit 420, the joint unit may be disposed in a manner that the yaw axis and the pitch axis are alternately provided. When the yaw axis and the pitch axis are alternately provided, a movable range of the arm unit 420 can be wider. Accordingly, when a task of requesting a wider movable range is performed, the arm unit 420 is preferably configured in a manner that the yaw axis and the pitch axis are alternately provided.

On the other hand, as illustrated in FIG. 4, when the pitch axis is provided to be continuous in a part of the arm unit 420, the arm unit 420 can be operated to be folded according to rotation about the pitch axis. When the arm unit 420 is operated to be folded, the arm unit 420 can be easily operated not to interfere with a predetermined area in a space. Accordingly, as in ensuring a visual field area of the operator exemplified above, when a task of requesting that the arm unit 420 is prevented from being in a predetermined area in a space is performed, as illustrated in FIG. 4, the arm unit 420 is preferably configured in a manner that a portion in which the pitch axis is provided to be continuous is present in at least a part thereof.

In addition, examples illustrated in FIGS. 1, 3, and 4, while the joint units 421e and 421f (the fifth axis $O_5$ and the sixth axis $O_6$) are treated as a redundant axis, the present embodiment is not limited thereto. When driving of the arm unit 420 is controlled, which of the plurality of joint units 421a to 421h is treated as a redundant axis may be appropriately set according to a type of a task performed by the support arm device 400.

In addition, as described above, the actuator 430 provided at each of the joint units 421a to 421h may be configured in a manner that a viscosity resistance coefficient in the rotating operation can be regulated. Using such a configuration, according to a type of the task performed by the support arm device 400, and in consideration of operability of the user, the viscosity coefficient may be changed for each of the joint units 421a to 421h. For example, when the first task is maintaining a viewpoint of the imaging unit 423 and the second task is ensuring a visual field area of the operator, a joint unit corresponding to an axis of rotation for performing the second task among the joint units 421a to 421h, that is, only a joint unit corresponding to the redundant axis may have a viscosity coefficient that is regulated to a small value. In this case, this is considered preferable, in order to perform the first task, rotation about an axis of rotation for performing the first task is preferably set so as not to be easily performed by a direct manipulation by the user in a manner that the position and the orientation of the imaging unit 423 are less likely to be changed, and in order to perform the second task, rotation about an axis of rotation (that is, a redundant axis) for performing the second task is easily performed by a direct manipulation in a manner that a part (a part that can interfere with a field of view) of the arm unit 420 can be easily moved.

In addition, in the arm unit 420, the actuator 430 need not be provided at all of the joint units 421a to 421h. In this case, a rotary shaft corresponding to a joint unit at which the actuator 430 is provided can be considered as a driving shaft that actively rotates along with driving of the actuator 430, and a rotary shaft corresponding to other joint unit can be considered as a passive shaft that is driven by rotation of the driving shaft to rotate. Which of the plurality of joint units 421a to 421h is configured as the passive shaft may be appropriately set in a manner that a task can be performed according to a type of the task performed by the arm unit 420. When some joint units are configured as the passive shaft, it is possible to provide the arm unit 420 in a small size at a low cost.

(2. Functional Configuration of Support Arm Device)
(2-1. Overview of Control)

Before a functional configuration of the support arm device 400 according to the present embodiment is described, an overview of processes performed to control the support arm device 400 will be described. Here, as an example, an overview of processes when the arm unit 420 is driven due to the force control will be described. Also, processes for controlling the support arm device 400 to be described below are only examples. In the present embodiment, driving of the arm unit 420 of the support arm device 400 may be controlled to simultaneously perform a plurality of tasks using a redundant degree of freedom, and a specific control method thereof is not limited. When driving of the arm unit 420 is controlled, various known control theories may be used.

In the present embodiment, driving of each of the joint units 421a to 421h of the support arm device 400 is controlled by a general cooperative control using generalized inverse dynamics. In this case, a command value corresponding to each of the joint units 421a to 421h is calculated in a manner that the plurality of tasks are simultaneously performed. Furthermore, an ideal joint control in which an influence of disturbance is corrected, and thereby an ideal response corresponding to the command value is implemented, is applied to drive control of each of the joint units 421a to 421h. Overviews of the generalized inverse dynamics and the ideal joint control will be sequentially described below.

(2-1-1. About Generalized Inverse Dynamics)

Generalized inverse dynamics refer to basic computation in a general cooperative control of a multi-link structure in which tasks related to various dimensions in various operation spaces are converted into torques generated in a plurality of joint units in consideration of various constraint conditions, in the multi-link structure (for example, the arm unit 420 illustrated in FIG. 1 in the present embodiment) in which a plurality of links are linked to each other by joint units.

The operation space is an important concept in the force control of the multi-link structure. The operation space is a space for describing a relation between a force applied to the multi-link structure and an acceleration of the multi-link structure. When drive control of the multi-link structure is performed by the force control rather than the position control, a concept of the operation space is necessary when a contact method of the multi-link structure and an environment is used as constraint conditions. The operation space is, for example, a space to which the multi-link structure belongs, a joint space, a Cartesian space, a momentum space, or the like.

A task (a movement purpose) is used to represent a purpose in the drive control of the multi-link structure. As the task, for example, "maintaining a viewpoint of an imaging unit" or "ensuring a field of view of an operator" may be set. In the actual control, more specifically, target values such as a position, a speed, an acceleration, a force, and an impedance of the multi-link structure may be set in order to accomplish such a task.

The constraint conditions refer to constraint conditions of a shape or a structure of the multi-link structure, and a position, a speed, an acceleration, and a force of the multi-link structure that are determined according to a nearby environment of the multi-link structure and settings by the user. For example, the constraint conditions include information on a generated force, a priority, whether or not a non-drive joint is provided, a vertical reaction force, a friction weight, a support polygon, and the like.

In the present embodiment, while the plurality of tasks may be set for the arm unit 420, constraint conditions necessary for implementing each of the tasks may be appropriately set according to each of the tasks. For example, when the task is "maintaining a viewpoint of an imaging unit," as constraint conditions thereof, geometric limitations on a tip position and a tip orientation are applied in a manner that a leading end position (a tip position) and a leading end orientation (a tip orientation) of the arm unit 420 are maintained in a predetermined state. In addition, for example, when the task is "ensuring a field of view of an operator," as constraint conditions thereof, limitations on a movable range are applied in a manner that the arm unit 420 does not enter a predetermined intrusion prohibition area set in a space. An area assumed to be a visual field area of the operator is set as the intrusion prohibition area.

In generalized dynamics, in order to accomplish both a stability of numerical calculation and real-time processable computation efficiency, an arithmetic algorithm thereof includes a virtual force determining process (a virtual force calculating process) serving as a first stage and an actual force conversion process (an actual force calculating process) serving as a second stage. In the virtual force calculating process serving as the first stage, a virtual force that is a force necessary to accomplish each task and virtually applied to the operation space is determined in consideration of a priority of the task and a maximum value of the virtual force. In the actual force calculating process serving as the second stage, the obtained virtual force is converted into an actual force that can be implemented in a configuration of an actual multi-link structure such as a joint force and an external force, in consideration of constraints of a non-drive joint, a vertical reaction force, a friction weight, a support polygon, or the like. Hereinafter, the virtual force calculating process and the actual force calculating process will be described in detail.

(2-1-1-1. Virtual Force Calculating Process)

A vector of physical quantities in the joint units of the multi-link structure is referred to as a general variable q (also referred to as a joint value q or a joint space q). An operation space x is defined by the following Expression (3) using the general variable q and a Jacobian J.

[Math.3]

$$\dot{x} = J\dot{q} \tag{3}$$

Here, Expression (3) represents the above-described Expression (1) in a further abstract manner. As shown in Expression (1), in the present embodiment, for example, x denotes leading end positions of the links 422a to 422h of the arm unit 420, and q denotes rotation angles of the joint units 421a to 421h of the arm unit 420. A movement equation of the operation space x is shown in the following Expression (4).

[Math.4]

$$\ddot{x} = \Lambda^{-1} f + c \tag{4}$$

Here, f denotes a force applied to an operation space x. In addition, $\Lambda^{-1}$ denotes an operation space inertia inverse matrix, and c is referred to as an operation space bias acceleration, which are represented by the following Expressions (5) and (6).

[Math.5]

$$\Lambda^{-1} = J H^{-1} J^T \tag{5}$$

$$c = J H^{-1}(\tau - b) + \dot{J}\dot{q} \tag{6}$$

Here, H denotes a joint space inertia matrix, τ denotes a joint force (for example, a generated torque in the joint units 421a to 421h) corresponding to a joint value q, and b is an item representing gravity, a Coriolis force, or a centrifugal force.

In generalized inverse dynamics, a target value of a position and speed related to the operation space x corresponding to the task is known to be represented as an acceleration of the operation space x. In this case, based on Expression (3), in order to implement an operation space acceleration which is a target value assigned according to the task, a virtual force to be applied to the operation space x is obtained by solving a kind of a linear complementary problem (LCP) such as the following Expression (7).

[Math. 6]

$$w + \ddot{x} = \Lambda^{-1} f_v + c \tag{7}$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ denote a negative lower limit value (including $-\infty$) of an i-th component of $f_v$ and a positive upper limit value (including $+\infty$) of the i-th component of $f_v$, respectively. The LCP can be solved using, for example, an iterative method, a pivot method, or a method in which a robust acceleration control is applied.

Also, when an operation space inertia inverse matrix $\Lambda^1$ and a bias acceleration c are calculated by Expressions (5) and (6) serving as definition equations, a calculation cost is high. Accordingly, a method in which a calculating process of the operation space inertia inverse matrix $\Lambda^{-1}$ is performed at a higher speed by applying quasi-dynamics calculation (FWD) through which a generalized acceleration (a joint acceleration) is obtained from a generalized force (a joint force τ) of the multi-link structure is proposed. Specifically, when forward dynamics calculation FWD is used, the operation space inertia inverse matrix $\Lambda^-$ and the bias acceleration c can be obtained from information on a force applied to the multi-link structure (for example, the arm unit 420) such as a joint space q, a joint force τ, and a gravity g. In this manner, when forward dynamics calculation FWD related to the operation space is applied, it is possible to calculate the operation space inertia inverse matrix $\Lambda^{31}$ at an amount of calculation of O(N) with respect to the number of joint units N.

Here, as setting an example of a target value corresponding to the task, conditions for accomplishing a target value (is denoted by adding a superscript bar to a second order derivative of x) of an operation space acceleration at the virtual force $f_{v_i}$ equal to or less than an absolute value $F_i$ can be represented by the following Expression (8).

[Math.7]

$$L_i = -F_i,$$

$$U_i = F_i,$$

$$\ddot{x}_i = \bar{\ddot{x}}_i \tag{8}$$

In addition, as described above, a target value of a position and speed of the operation space x can be represented as a target value of the operation space acceleration, and specifically, represented by the following Expression (9) (target values of a position and a speed of the operation space x are represented by x and by adding a superscript bar to a first order derivative of x).

[Math.8]

$$\bar{\ddot{x}}_i = K_p(\bar{x}_i - x_i) + K_v(\bar{\dot{x}}_i - \dot{x}_i) \tag{9}$$

In addition, a target value of an operation space (such as a momentum, relative Cartesian coordinates, and an interlocking joint) represented by a linear sum of other operation spaces can be set using a concept of a decomposed operation space.

Here, in the present embodiment, when a plurality of tasks are assigned, a priority is set. Therefore, when tasks conflict, the virtual force is calculated based on the priority. According to a method in which the above LCP is solved to obtain the virtual force $f_v$, for example, the LCP is solved for each priority in order from a low priority, and a virtual force obtained in a proceeding stage LCP can be applied as a known external force of the next stage LCP.

(2-1-1-2. Actual Force Calculating Process)

In the actual force calculating process serving as the second stage of generalized inverse dynamics, a process in which the virtual force obtained in the above (2-1-1-1. Virtual Force Calculating Process) is replaced with an actual joint force and an external force is performed. Conditions for implementing a generalized force $\tau_v = J_v^T f$, according to a virtual force with a generated torque $\tau_a$ generated in the joint unit and an external force $f_e$ are represented by the following Expression (10).

[Math. 9]

$$\begin{bmatrix} J_{vu}^T \\ J_{va}^T \end{bmatrix} (f_v - \Delta f_v) = \begin{bmatrix} J_{eu}^T \\ J_{ea}^T \end{bmatrix} f_e + \begin{bmatrix} 0 \\ \tau_a \end{bmatrix} \quad (10)$$

Here, a subscript a denotes a set of drive joint units (a drive joint set), and a subscript u denotes a set of non-drive joint units (a non-drive joint set). That is, an upper part of Expression (10) represents a balance of a force of a space (a non-drive joint space) according to a non-drive joint unit, and a lower part thereof represents a balance of a force of a space (a drive joint space) according to a drive joint unit. $J_{vu}$ and $J_{va}$ denote a Jacobian non-drive joint component and a Jacobian drive joint component related to an operation space in which the virtual force $f_v$ is applied, respectively. $J_{eu}$ and $J_{ea}$ denote a Jacobian non-drive joint component and a Jacobian drive joint component related to an operation space in which the external force $f_e$ is applied. $\Delta f_v$ denotes a component that is infeasible with an actual force within the virtual force $f_v$.

The upper part of Expression (10) is undefined. For example, when a quadratic programming problem (QP) shown in the following Expression (11) is solved, $f_e$ and $\Delta f_v$ can be obtained.

[Math.10]

$$\min \tfrac{1}{2} \varepsilon^T Q_1 \varepsilon + \tfrac{1}{2} \zeta^T Q_2 \zeta \, s.t. \, U \zeta \le v \quad (11)$$

Here, ε is a difference between both sides of the upper part of Expression (10), and denotes an equality error of Expression (10). ζ is a vector connecting $f_c$ and $\Delta f_v$, and denotes a variable vector. $Q_1$ and $Q_2$ denote a positive definite value symmetric matrix representing weights when minimization is performed. In addition, inequality constraints of Expression (11) are used to represent constraint conditions of the external force such as a vertical reaction force, a friction weight, a maximum value of an external force, and a support polygon.

For example, inequality constraints of a rectangular support polygon are represented by the following Expression (12).

[Math.11]

$|F_x| \le \mu_t F_z$, $|F_y| \le \mu_t F_z$, $F_z \le 0$, $|M_x| \le d_y F_z$, $|M_y| \le d_x F_z$, $|M_z| \le \mu_r F_z \quad (12)$ Here, z denotes a normal direction of a contact surface, and x and y denote two vertical tangential directions orthogonal to z. ($F_x$, $F_y$, $F_z$) and ($M_x$, $M_y$, $M_z$) denote an external force and an external force moment applied to a contact point. $\mu_t$ and $\mu_r$ denote friction coefficients of translation and rotation, respectively. ($d_x$, $d_y$) denotes a size of a support polygon.

Based on Expressions (11) and (12), solutions $f_e$ and $\Delta f_v$ of a minimum norm and a minimum error are obtained. When $f_e$ and $\Delta f_v$ obtained from Expression (11) are assigned to the lower part of Expression (10), it is possible to obtain a joint force $\tau_a$ that is necessary to implement the task.

Actually, constraint conditions corresponding to each set task are appropriately formulated and set as shown in Expression (12).

In a system in which a base is fixed and no non-drive joint is included, all virtual forces can be replaced with only the joint force. In Expression (10), $f_e = 0$, and $\Delta f_v = 0$ can be set. In this case, it is possible to obtain the following Expression (13) of the joint force $\tau_a$ from the lower part of Expression (10).

[Math.12]

$$\tau_a = J_{va}^T f_v \quad (13)$$

The general cooperative control using generalized inverse dynamics according to the present embodiment has been described above. As described above, when the virtual force calculating process and the actual force calculating process are sequentially performed, it is possible to obtain the joint force $\tau_a$ for accomplishing a desired task. That is, on the other hand, when the calculated joint force $\tau_a$ is applied to a theoretical model in a movement of the joint units 421a to 421h, the joint units 421a to 421h are driven to accomplish the desired task.

Also, the general cooperative control using generalized inverse dynamics described above, in particular, details of a deriving process of the virtual force $f_v$, a method in which the LCP is solved and the virtual force is determined, a solution of QP problems, and the like can refer to for example, JP 2009-95959A and JP 2010-188471A which are prior patent applications of the applicants.

(2-1-2. About Ideal Joint Control)

Next, an ideal joint control according to the present embodiment will be described. A movement of the actuator 430 provided at each of the joint units 421a to 421h of the support arm device 400 is modeled by a movement equation of a secondary delay system shown in the following Expression (14).

[Math.13]

$$I_a \ddot{q} = \tau_a + \tau_e - \nu_a \dot{q} \quad (14)$$

Here, q denotes a rotation angle of the actuator 430, $q_{ref}$ denotes a rotation angle target value of the actuator 430, $I_a$ denotes an inertia moment (inertia) of the actuator 430, $\tau_a$ denotes a generated torque of the actuator 430, $\tau_e$ denotes an external torque applied to the actuator 430 from the outside, and $\nu_a$ denotes a viscosity resistance coefficient of the actuator 430. Expression (14) is a theoretical model representing a movement of the actuator 430 at each of the joint units 421a to 421h.

As described in the above (2-1-1. About Generalized Inverse Dynamics), according to computation using generalized inverse dynamics, it is possible to calculate a torque $\tau_a$ (a generated torque $\tau_a$) to be generated by the actuator 430 of each of the joint units 421a to 421h to implement the task. Accordingly, ideally, when the generated torque $\tau_a$ calculated with respect to each of the actuators 430 is applied to Expression (14), a response according to the theoretical model shown in Expression (14) in each of the actuators 430 is implemented, that is, a desired operation in the arm unit 420 is implemented.

However, actually, due to influences of various disturbances, an error (a modeling error) between an actual movement in the actuator 430 and the theoretical model shown in Expression (14) may occur. The modeling error can be broadly classified as an error due to mass properties such as a weight of the multi-link structure (that is, the arm unit 420 to be controlled), a center of gravity, and an inertia tensor, or an error due to friction and inertia inside the actuator 430. Among these, the former modeling error caused by the mass properties can be relatively easily reduced according to highly accurate computer aided design (CAD) data and an application of an identification technique when the theoretical model is constructed.

On the other hand, the latter modeling error caused by friction and inertia inside the actuator 430 is caused by a phenomenon that is difficult to be modeled, for example, friction in the decelerator 426. Accordingly, when a theoretical model representing a movement of the actuator 430 is constructed, unignorable modeling errors may remain. In addition, there is a possibility of an error between values of an inertia $I_a$ and a viscosity resistance coefficient $v_a$ in Expression (14) and such values in the actual actuator 430. Such errors caused by friction and inertia inside the actuator 430, which are difficult to be modeled, may serve as a disturbance in the drive control of the actuator 430. Therefore, due to an influence of such a disturbance, a movement of the actuator does not actually correspond to the theoretical model shown in Expression (14), that is, a case in which a desired operation is not implemented occurs.

Accordingly, in the present embodiment, when an active control system is added to the actuator 430, a response of the actuator 430 is corrected to perform an ideal response according to the theoretical model shown in Expression (14). Also, in this manner, controlling, by the actuator 430 of the support arm device 400 (that is, the joint units 421a to 421h), driving of the actuator 430 to perform an ideal response as shown in Expression (14) is referred to as an ideal joint control in the present embodiment.

An ideal joint control according to the present embodiment will be described in detail with reference to FIG. 5. FIG. 5 is a diagram for describing an ideal joint control according to the present embodiment. FIG. 5 schematically illustrates a conceptual computing unit configured to perform various types of computation according to the ideal joint control in blocks. Also, a block diagram illustrated in FIG. 5 shows a series of processes in the ideal joint control with respect to the actuator 430 of one joint unit among the joint units 421a to 421h of the support arm device 400.

As illustrated in FIG. 5, an actuator 610 shows a mechanism of, for example, the actuator 430 illustrated in FIG. 2 in a simulated manner. In FIG. 5, a motor 611, a decelerator 612, an encoder 613, and a torque sensor 614 are illustrated as components of the actuator 610, and these respectively correspond to the motor 424, the decelerator 426, the encoder 427, and the torque sensor 428 illustrated in FIG. 2.

A computing unit 631 is a computing unit configured to perform computation according to the ideal joint model of the actuator 610 (that is, the joint units 421a to 421h) shown in Expression (14). The computing unit 631 can output a rotation angular acceleration target value (a second order derivative of a rotation angle target value $q^{ref}$) shown in the left-hand side of Expression (14) using a generated torque $\tau_a$, an external torque $\tau_e$, and a rotation angular velocity (a first order derivative of a rotation angle q) as inputs.

Here, performing, by the actuator 610, a response according to the theoretical model shown in Expression (14) refers to accomplishment of the rotation angular acceleration of the left-hand side when the right-hand side of Expression (14) is given. However, as described above, due to an influence of a disturbance, an ideal response according to Expression (14) is not actually generated. Therefore, in the present embodiment, a disturbance observer 620 is introduced. The disturbance observer 620 calculates a disturbance estimation value $\tau_d$ which is an estimated value of a torque caused by a disturbance and performs a process of correcting a result of the calculation by the computing unit 631 using the disturbance estimation value $\tau_d$.

Hereinafter, specific processes will be sequentially described. First, the generated torque $\tau_a$ for implementing a desired task, which is calculated by the method described in the above (2-1-1. About Generalized Inverse Dynamics) and the external torque $\tau_e$ detected by the torque sensor 614 are input to the computing unit 631. On the other hand, when a rotation angle q of the actuator 610 detected by the encoder 613 is input to a computing unit 632 configured to perform a differential operation, a rotation angular velocity (a first order derivative of the rotation angle q) of the actuator 610 is calculated. In addition to the generated torque $\tau_a$ and the external torque $\tau_e$, when the rotation angular velocity calculated by the computing unit 632 is input to the computing unit 631, a rotation angular acceleration target value (a second order derivative of $q^{ref}$) is calculated by the computing unit 631. The calculated rotation angular acceleration target value is input to a computing unit 633.

The computing unit 633 is a computing unit configured to calculate a torque generated in the actuator 610 based on a rotation angular acceleration of the actuator 610. In the present embodiment, specifically, the computing unit 633 multiplies the rotation angular acceleration target value calculated by the computing unit 631 by a nominal inertia $J_n$ of the actuator 610 to calculate a torque target value $\tau^{ref}$. In an ideal response, when the actuator 610 is driven to output the torque target value $\tau^{ref}$ a desired operation is implemented. However, as described above, the influence of a disturbance or the like occurs in an actual response. Accordingly, in the present embodiment, the disturbance estimation value $\tau_d$ calculated by the disturbance observer 620 is used to correct the torque target value $\tau^{ref}$.

A configuration of the disturbance observer 620 will be described. The disturbance observer 620 calculates the disturbance estimation value $\tau_d$ based on the torque command value $\tau$ and the rotation angular velocity calculated from the rotation angle q of the actuator 610 detected by the encoder 613. Here, the torque command value $\tau$ is a command value that is ultimately assigned to the actuator 610 after the influence of a disturbance is corrected. That is, in a control system illustrated in FIG. 5, the actuator 610 is driven to output a torque corresponding to the torque command value $\tau$. For example, when the disturbance estimation value $\tau_d$ is substantially zero, the torque command value $\tau$ is substantially equal to the torque target value $\tau^{ref}$.

Specifically, the disturbance observer 620 includes a computing unit 634 and a computing unit 635. The computing unit 634 is a computing unit configured to calculate a torque generated in the actuator 610 based on the rotation angular velocity of the actuator 610. A rotation angular velocity calculated by the computing unit 632 based on the rotation angle q detected by the encoder 613 is input to the computing unit 634. The computing unit 634 calculates an estimation value (a torque estimation value) of a torque that is actually applied to the actuator 610 by performing computation represented by a transfer function $J_n s$ with respect to the input rotation angular velocity, that is, obtaining a rotation angular acceleration by differentiating the rotation angular velocity and further multiplying the calculated rotation angular acceleration by a nominal inertia $J_n$.

Inside the disturbance observer 620, when a difference between the torque estimation value and the torque command value τ is obtained, the disturbance estimation value $\tau_d$, which is a torque value due to a disturbance, is estimated. Specifically, the disturbance estimation value $\tau_d$ refers to a difference between a torque command value τ in the control of the previous step and a torque estimation value in control of a current step. The torque estimation value calculated by the computing unit 634 is based on an actual measurement value, and the torque command value τ calculated by the computing unit 633 is based on an ideal theoretical model of the actuator 610 calculated by the computing unit 631. Therefore, when a difference between two values is obtained, it is possible to estimate the influence of a disturbance that is not considered in the theoretical model.

The computing unit 635 is a computing unit that is provided to prevent divergence of a system and includes a function of a low pass filter (LPF). The computing unit 635 performs computation represented by a transfer function $g/(s+g)$, outputs only a low frequency component of an input value, and stabilizes the system. A difference value between the torque estimation value calculated by the computing unit 634 and the torque target value $\tau^{ref}$ is input to the computing unit 635, and the low frequency component is calculated as the disturbance estimation value $\tau_d$.

When the disturbance estimation value $\tau_d$ is calculated by the disturbance observer 620, the disturbance estimation value $\tau_d$ is added to the torque target value $\tau^{ref}$ which is a theoretical value, and the torque command value τ, which is a torque value ultimately generated in the actuator 610, is calculated. The calculated torque command value τ is input to a block 636 representing a joint unit. The block 636 represents the joint units 421a to 421h (that is, the actuator 610) in a simulated manner. In the block 636, the actuator 610 is driven based on the torque command value τ. Specifically, in the block 636, when the torque command value τ is converted into a corresponding current value (a current command value), and the current command value is applied to the motor 611, the actuator 610 is driven to output a torque corresponding to the torque command value τ.

When the above-described processes are performed on the actuator 430 of each of the joint units 421a to 421h constituting the arm unit 420 of the support arm device 400, an operation of the arm unit 420 may be controlled with high accuracy in a manner that each of the actuators 430 has an ideal response according to the theoretical model, and the arm unit 420 implements a desired task.

The ideal joint control according to the present embodiment has been described above with reference to FIG. 5. When the above-described configuration is applied, in the drive control of the joint units 421a to 421h according to the present embodiment, it is possible to cause a response of the actuator 610 to follow the target value even in a case in which there is a disturbance component of friction or the like.

Also, details of the above-described ideal joint control can refer to, for example, JP 2009-269102A which is a prior patent application of the applicants.

(2-2. Functional Configuration)

A functional configuration of the support arm device 400 according to the present embodiment illustrated in FIG. 1 will be described with reference to FIG. 6. FIG. 6 is a functional block diagram illustrating an exemplary functional configuration of a support arm device according to the present embodiment. Also, FIG. 6 illustrates a functional configuration of an observation system including a support arm device and a display device on which an image captured by an imaging unit of the support arm device is displayed.

As illustrated in FIG. 6, an observation system 1 according to the present embodiment includes a support arm device 10 and a display device 30. In addition, the support arm device 10 includes an arm unit 110, an imaging unit 140, and a control device 210.

The arm unit 110, the imaging unit 140, and the control device 210 illustrated in FIG. 6 respectively correspond to the arm unit 420, the imaging unit 423, and the control device 440 illustrated in FIG. 1. Note that, similarly to the configuration illustrated in FIG. 1, the arm unit 110 actually includes a plurality of links and a plurality of joint units. However, FIG. 6 representatively illustrates a functional configuration of only one joint unit 130. Other joint units 130 (not illustrated) also have the same functional configuration. In addition, similarly to the configuration illustrated in FIG. 1, the imaging unit 140 is actually attached at a leading end of the arm unit 110. However, in FIG. 6, a state in which the imaging unit 140 is attached at the leading end of the arm unit 110 is represented by schematically illustrating a link of the arm unit 110 between the joint unit 130 and the imaging unit 140.

(Display Device 30)

The display device 30 is a device that displays various types of information on a display screen in various formats such as text and an image, and thereby visually notifies the user of the various types of information. In the present embodiment, the display device 30 is installed in the operating room, and displays an image of the operation part captured by the imaging unit 140 of the support arm device 10. In this case, the display device 30 may display the captured image of the operation part that is enlarged at an appropriate magnification. The operator performs various processes on the operation part while referring to the image of the operation part displayed on the display device 30.

For example, the display device 30 includes functions of an image signal processing unit (not illustrated) configured to perform various types of image processing on the image signal acquired by the imaging unit 140 and a display control unit (not illustrated) configured to perform control in a manner that the image is displayed on the display screen based on the processed image signal. In addition, the display device 30 may have various functions of a general display device.

Specifically, as the display device 30, various known display devices, for example, a cathode ray tube (CRT) display device, a liquid crystal display device, a plasma display device, and an electro-luminescence (EL) display device, may be used. In addition, communication between the imaging unit 140 and the display device 30 may be implemented by various known wired or wireless methods.

Note that, the image processing on the image signal described above may not necessarily be performed in the display device 30. For example, a processing circuit configured to perform the above image processing may be provided in the imaging unit 140 and the above image processing may be performed by the processing circuit of the imaging unit 140. Alternatively, the image signal acquired by the imaging unit 140 is temporarily provided to the control device 210 and the above image processing may be performed by the control device 210.

(Support Arm Device 10)

(Imaging Unit 140)

The imaging unit 140 is an example of the observation unit that is used to observe the operation part, and is configured as, for example, a camera capable of imaging a video and/or a still image of an imaging target. The imaging unit 140 may be a so-called video microscope. The imaging unit 140 is attached at the leading end of the arm unit 110. When driving of the arm unit 110 is controlled, a position and an orientation of the imaging unit 140 is controlled in a manner that the imaging unit 140 images the patient's operation part, which is an observation target.

The image signal of the operation part captured by the imaging unit 140 is transmitted to the display device 30. Based on information on the transmitted image, the image of the patient's operation part is displayed on the display device 30. Also, since configurations of various known video microscopes can be applied as a specific configuration of the imaging unit 423, details thereof will be omitted herein.

(Joint Unit 130 of Arm Unit 110)

The joint unit 130 of the arm unit 110 includes functions of a joint drive unit 131 and a joint state detecting unit 132.

The joint drive unit 131 is a drive mechanism for driving the joint unit 130 to rotate. The joint drive unit 131 corresponds to, for example, the motor 424 and the motor driver 425 of the actuator 430 illustrated in FIG. 2.

Driving of the joint drive unit 131 is controlled by a drive control unit 260 of the control device 210 to be described below. Specifically, a value of a torque (the torque command value τ illustrated in FIG. 5) to be generated by the joint unit 130 to implement a desired task is calculated by an ideal joint control unit 250 of the control device 210 to be described below. The drive control unit 260 provides a current command value corresponding to the calculated torque command value τ to the joint drive unit 131, and issues an instruction to the joint drive unit 131 in a manner that the motor 424 is driven according to the current command value. When the motor 424 of the joint drive unit 131 is driven according to the current command value, the joint unit 130 is driven in a manner that a torque is generated according to the torque command value.

The joint state detecting unit 132 detects a state of the joint unit 130. Here, a state of the joint unit 130 refers to a movement state of the joint unit 130. The state of the joint unit 130 includes information on, for example, a rotation angle, a rotation angular velocity, a rotation angular acceleration, and a generated torque of the joint unit 130.

The joint state detecting unit 132 includes a rotation angle detecting unit 133 configured to detect a rotation angle of the joint unit 130 and a torque detecting unit 134 configured to detect a torque applied to the joint unit 130. The rotation angle detecting unit 133 and the torque detecting unit 134 correspond to the encoder 427 and the torque sensor 428 of the actuator 430 illustrated in FIG. 2, respectively.

The joint state detecting unit 132 provides information on the detected state of the joint unit 130 to an arm state acquisition unit 241 of the control device 210 to be described below.

(Control Device 210)

The control device 210 includes functions of a general cooperative control unit 240, the ideal joint control unit 250, and the drive control unit 260. When a processor of the control device 210 is operated according to a predetermined program, these functions are implemented.

(General Cooperative Control Unit 240)

The general cooperative control unit 240 performs various types of computation related to the general cooperative control using generalized inverse dynamics. The general cooperative control unit 240 includes functions of the arm state acquisition unit 241, a computation condition setting unit 242, a virtual force calculating unit 243, and an actual force calculating unit 244. Note that, processes performed by the general cooperative control unit 240 correspond to the series of processes described in the above (2-1-1. About Generalized Inverse Dynamics).

The arm state acquisition unit 241 acquires a state (an arm state) of the arm unit 110 based on the state of the joint unit 130 detected by the joint state detecting unit 132. Here, the arm state refers to a movement state of the arm unit 110. For example, the arm state includes information on a position, a speed, an acceleration, and a force of the arm unit 110. When the arm state is acquired, current positions and orientations of the arm unit 110 and the imaging unit 140, forces that are currently applied to the arm unit 110, the imaging unit 140, and the like may be determined.

As described above, the joint state detecting unit 132 acquires information on a rotation angle, a rotation angular velocity, a rotation angular acceleration, and a generated torque in each of the joint units 130 as the state of the joint unit 130. In addition, a storage unit (not illustrated) configured to store various types of information to be processed by the control device 210 is provided in the control device 210. An internal model of the arm unit 110 is stored in the storage unit. Here, the internal model is a control model used in drive control of the support arm device 10, and includes information (geometric information) representing a position and an orientation of the arm unit 110 to be controlled. The control device 210 can acquire a current arm state based on the state of the joint unit 130 and the internal model.

The arm state acquisition unit 241 provides the information on the acquired arm state to the computation condition setting unit 242.

The computation condition setting unit 242 sets computation conditions for calculating a control value (the above-described generated torque $\tau_a$) for drive control of the arm unit 110 (that is, for drive control of the joint unit 130). As the computation conditions, a target value of a position of the operation space x according to a task to be performed in the arm unit 110 or the task described in the above (2-1-1. About Generalized Inverse Dynamics), and constraint conditions according to a corresponding task are set. In the present embodiment, the computation condition setting unit 242 sets a plurality of tasks and constraint conditions corresponding to the plurality of tasks.

For example, in the storage unit (not illustrated) provided in the control device 210, combinations of various tasks that can be set for the drive control of the arm unit 110 and constraint conditions corresponding to such various tasks are stored in advance. When the computation condition setting unit 242 accesses the storage unit, any of such tasks and constraint conditions can be set as computation conditions.

In FIG. 6, as tasks and constraint conditions that may be set by the computation condition setting unit 242, a first task (a movement purpose 1) and a constraint condition 1 corresponding to the first task, and a second task (a movement purpose 2) and a constraint condition 2 corresponding to the second task are illustrated in a simulated manner.

Actually, a task to be performed by the arm unit 110 may be appropriately set by the user through, for example, an input unit (not illustrated) provided in the control device 210. The computation condition setting unit 242 can set predetermined task and constraint conditions as computation conditions according to an instruction input by the user.

The computation condition setting unit 242 provides information on the arm state and information on the set movement purpose and constraint conditions to the virtual force calculating unit 243.

The virtual force calculating unit 243 calculates a virtual force that is necessary to perform the task set by the computation condition setting unit 242 and applied to each of the joint units 130 of the arm unit 110. For example, the virtual force calculating unit 243 calculates a virtual force by performing the series of processes described in the above (2-1-1-1. Virtual Force Calculating Process).

The virtual force calculating unit 243 provides information on the calculated virtual force to the actual force calculating unit 244.

The actual force calculating unit 244 calculates an actual force that is necessary to perform the task set by the computation condition setting unit 242 and actually applied to each of joint units 130 of the arm unit 110 based on the virtual force calculated by the virtual force calculating unit 243. For example, the actual force calculating unit 244 calculates an actual force by performing the series of processes described in the above (2-1-1-2. Actual Force Calculating Process).

As described in the above (2-1-1-2. Actual Force Calculating Process), the actual force calculated by the actual force calculating unit 244 may be the generated torque $\tau_a$ to be generated by the joint unit 130. The actual force calculating unit 244 provides information on the calculated generated torque $\tau_a$ to the ideal joint control unit 250. Note that, in the present embodiment, the generated torque $\tau_a$ calculated by the actual force calculating unit 244 is also called a control value, which refers to a control value of the joint unit 130 in the general cooperative control.

(Ideal Joint Control Unit 250)

The ideal joint control unit 250 performs various types of computation related to an ideal joint control. The ideal joint control unit 250 includes functions of a disturbance estimating unit 251 and a command value calculating unit 252. Note that, processes performed by the ideal joint control unit 250 correspond to the series of processes described in the above (2-1-2. About Ideal Joint Control).

The disturbance estimating unit 251 includes a function corresponding to the disturbance observer 620 illustrated in FIG. 5. The disturbance estimating unit 251 obtains a difference between the torque command value $\tau$ (a torque value applied to the joint unit 130 determined according to the theoretical model of the joint unit 130 shown in Expression (14) based on the generated torque $\tau_a$ calculated by the actual force calculating unit 244 and an external torque value applied to the joint unit 130 detected by the rotation angle detecting unit 133) and a torque value applied to the joint unit 130 calculated based on a rotation angle of the joint unit 130 detected by the rotation angle detecting unit 133, and thereby calculates the disturbance estimation value $\tau_d$ which is a torque value due to a disturbance. Also, the torque command value $\tau$ herein is a command value indicating a torque that is ultimately generated in the joint unit 130 of the arm unit 110. The torque command value $\tau$ used by the disturbance estimating unit 251 to calculate the disturbance estimation value $\tau_d$ may be the torque command value $\tau$ in the control of the previous step.

The command value calculating unit 252 calculates the torque command value $\tau$ which is a command value indicating a torque that is ultimately generated in the joint unit 130 of the arm unit 110 using the disturbance estimation value $\tau_d$ calculated by the disturbance estimating unit 251. Specifically, the command value calculating unit 252 adds the disturbance estimation value $\tau_d$ calculated by the disturbance estimating unit 251 to the torque target value $\tau^{ref}$ calculated from the theoretical model of the joint unit 130 shown in Expression (14), and thereby calculates the torque command value $\tau$.

The command value calculating unit 252 provides information on the calculated torque command value $\tau$ to the drive control unit 260.

The drive control unit 260 controls driving of the joint drive unit 131 of the joint unit 130 in a manner that a torque corresponding to the torque command value $\tau$ is generated in the joint unit 130 based on the torque command value $\tau$ calculated by the command value calculating unit 252. Specifically, the drive control unit 260 can issue an instruction to the motor driver 425 of the joint drive unit 131 in a manner that the torque command value $\tau$ is converted into a corresponding current command value, and the motor 424 of the joint drive unit 131 is driven at a current according to the current command value.

When each of the joint units 130 of the arm unit 110 is driven in a manner that a torque corresponding to the torque command value $\tau$ calculated by the ideal joint control unit 250 is generated under control of the drive control unit 260, the arm unit 110 is driven to implement a desired task.

The observation system 1 according to the present embodiment, in particular, a functional configuration of the support arm device 10 has been described above.

Note that, the functional configuration illustrated in FIG. 6 is only an example of a functional configuration of the observation system 1 and the support arm device 10 according to the present embodiment. The functional configuration of the observation system 1 and the support arm device 10 is not limited thereto. The observation system 1 and the support arm device 10 may be configured to implement the functions described above, and can have any configuration that may be generally assumed.

For example, the support arm device 10 may include various functions of a general support arm device (an observation device) in addition to the illustrated functions. For example, as described above, the support arm device 10 may have functions of a storage unit configured to store various types of information processed by the support arm device 10 and an input unit configured to input, by the user, various types of information to the support arm device 10. The storage unit may be configured as various storage devices, for example, a magnetic storage device such as an HDD, a semi-conductor storage device, an optical storage device, and a magneto-optical storage device. In addition, the input unit may be configured as various input devices, for example, a mouse, a keyboard, a touch panel, a button, a switch, and a lever. Since functions (not illustrated) are similar to functions of the general support arm device (the observation device), details thereof will be omitted.

In addition, for example, all functions of the control device 210 of the support arm device 10 may not be performed in one device but may be performed by a cooperation of a plurality of devices. For example, when one device including only any one or a plurality of functions included in the general cooperative control unit 240, the ideal joint control unit 250, and the drive control unit 260 is communicatively connected to another device having other functions, the same functions of the illustrated control device 210 may be implemented.

In addition, a computer program for implementing functions of the observation system 1 according to the present embodiment illustrated in FIG. 6, particularly, the control device 210 of the support arm device 10, can be generated and implemented in a processing device such as a PC. In addition, a computer readable recording medium in which such a computer program is stored can be provided. The recording medium is, for example, a magnetic disk, an optical disc, a magneto-optical disc, or a flash memory. In addition, the above computer program may be distributed via, for example, a network, without using the recording medium.

(3. Specific Example of Tasks)

As described above, in the support arm device 10 according to the present embodiment, when drive control of the arm unit 110 is performed, the plurality of tasks are set and the arm unit 110 is driven to simultaneously implement such a plurality of tasks. As the task, for example, the following tasks are assumed. In the present embodiment, two or more tasks among tasks exemplified below may be set the task when the drive control of the arm unit 110 is performed.

(3-1. Maintaining Viewpoint of Imaging Unit)

When a task of "maintaining a viewpoint of an imaging unit" is set, driving of the arm unit 110 is controlled in a manner that a position and an orientation of the imaging unit 140 are not changed even if, for example, an external force is added. In this case, as constraint conditions, limitations are imposed on a tip position and a tip orientation of the arm unit 110 in a manner that the tip position and the tip orientation of the arm unit 110 are not changed from a current position and orientation.

(3-2. Pivot Operation)

When a task of "pivot operation" is set, driving of the arm unit 110 is controlled in a manner that the imaging unit 140 performs a pivot operation. Here, the pivot operation refers to an operation of moving on a conical surface using a predetermined point as a vertex while the imaging unit 140 constantly faces the predetermined point in a space (that is, while an optical axis of the imaging unit 140 constantly passes the predetermined point in a space). That is, in the pivot operation, the imaging unit 140 performs a turning operation using a conical axis whose vertex is a predetermined point in a space as a pivot axis. The predetermined point is also referred to as a pivot center since the point indicates a center in the pivot operation. When the predetermined point is set to the patient's operation part, since the imaging unit 140 is operated to turn around the operation part while imaging the operation part, it is possible to observe the operation part in various directions.

Note that, when the observation unit attached at the leading end of the arm unit 110 is an endoscope and the pivot operation is performed on the endoscope, the pivot center is set, for example, in the vicinity of an insertion opening of a trocar with respect to the patient's body. Accordingly, the endoscope performs the pivot operation using an insertion position as a center.

When the task of "pivot operation" is set, as constraint conditions, limitations are imposed on a position of the imaging unit 140 in a manner that the imaging unit 140 is constantly positioned on a conical surface in the pivot operation. In addition, limiitations are imposed on an orientation (a posture) of the imaging unit 140 in a manner that the imaging unit 140 constantly faces the pivot center. Note that, the "maintaining a viewpoint of an imaging unit" and the "pivot operation" correspond to tasks of controlling a position and an orientation of the imaging unit.

(3-3. Ensuring Visual Field Area)

When a task of "ensuring a visual field area" is set, driving of the arm unit 110 is controlled in a manner that the arm unit 110 does not block a field of view of the user. In this case, for example, as constraint conditions, limitations are imposed on a position and an orientation of the arm unit 110 in a manner that a predetermined area assumed to be a visual field area of the user in a space is set, and the arm unit 110 does not enter the visual field area. That is, the visual field area is set as an intrusion prohibition area and driving of the arm unit 110 is controlled so as not to enter the intrusion prohibition area. Accordingly, the field of view of the operator is not blocked, and the operator can perform surgery more smoothly. Also, a specific control method of the arm unit 110 when "ensuring a visual field area" is set will be described in detail in the following (5-1. When "ensuring a visual field area" is set as a task).

(3-4. Avoiding Specific Orientation)

When a task of "avoiding a specific orientation" is set, driving of the arm unit 110 is controlled in a manner that the arm unit 110 does not have a specific orientation. Here, the specific orientation refers to an orientation in which calculation diverges in control and it is not possible to obtain a stable control of the arm unit 110. For example, in the arm structure, a wrist-specific orientation, a shoulder-specific orientation, an elbow-specific orientation, and the like are known. The specific orientation is determined according to a configuration (such as the number of joints and a movable range) of the arm unit 110.

When the task of "avoiding a specific orientation" is set, as constraint conditions, limitations are imposed on the orientation of the arm unit 110 in a manner that the arm unit 110 does not have a specific orientation that is set in advance based on the configuration of the arm unit 110.

(3-5. Avoiding Mechanically Limited Orientation)

When a task of "avoiding a mechanically limited orientation" is set, driving of the arm unit 110 is controlled in a manner that the arm unit 110 does not have a mechanically impractical orientation (hereinafter referred to as a "mechanically limited orientation"). Since the joint units 130 constituting the arm unit 110 may have a rotatable range, the arm unit 110 may have a mechanically impractical orientation. When the task of "avoiding a mechanically limited orientation" is set, as constraint conditions, limitations are imposed on an orientation of the arm unit 110 in a manner that the arm unit 110 does not have a mechanically limited orientation that is set in advance based on the configuration of the arm unit 110. Note that, a specific control method of the arm unit 110 when "avoiding a mechanically limited orientation" is set will be described in detail in the following (5-2. When "avoiding a mechanically limited orientation" is set as a task).

(3-6. Energy Minimization)

When a task of "energy minimization" is set, driving of the arm unit 110 is controlled in a manner that as little energy is consumed as possible in the arm unit 110 when the orientation of the arm unit 110 is changed to perform another task. In this case, as candidates of the orientation of the arm unit 110 that may be implemented for other tasks, an amount of change in the rotation angle of each of the joint units 130 from a current orientation of the arm unit 110 is calculated, and driving of the arm unit 110 may be controlled in a manner that the arm unit 110 has an orientation in which an amount of change in the rotation angle is the smallest.

The specific examples of some tasks that may be set when driving of the arm unit 110 is controlled have been described above. In the present embodiment, some of the plurality of tasks exemplified above are combined with one another (when possible), and set for the drive control of the arm unit 110. Since the arm unit 110 is configured to have a redundant degree of freedom, driving of the arm unit 110 can be controlled in a manner that the plurality of set tasks are simultaneously performed. Accordingly, since the arm unit 110 can be caused to better perform an operation according to the user's demand, it is possible to increase user convenience.

In addition, in the present embodiment, driving of the arm unit 110 is appropriately controlled by the force control. Accordingly, the user can perform a manipulation more intuitively with high operability. In this manner, according to the present embodiment, a support arm device having higher operability when the plurality of tasks are simultaneously performed may be provided.

Also, a combination of tasks set for the arm unit 110 may be appropriately selected by the user according to an application of the support arm device 10 or the like. For example, "maintaining a viewpoint of an imaging unit" and "ensuring a visual field area" may be appropriately set as the first task and the second task. In addition, as another example, "pivot operation" and "avoiding a specific orientation" may be appropriately set as the first task and the second task.

Note that, the above-described tasks are only examples. In the present embodiment, other tasks may be set for the arm unit 110. Various tasks set when driving of the arm unit of the general support arm device is controlled may be set for the arm unit 110.

In addition, a task set for the arm unit 110 may be appropriately selected according to an application of the support arm device 10, in particular, a type of the medical instrument provided at the leading end of the arm unit 110. For example, when the endoscope is attached at the leading end of the arm unit 110, a task of indicating holding an insertion position of the endoscope in the patient's body is set, and driving of the arm unit 110 may be controlled in a manner that the insertion position of the endoscope is not changed from a current state.

(4. Method of Controlling Support Arm Device)

A processing procedure of a method of controlling a support arm device according to the present embodiment will be described with reference to FIG. 7. FIG. 7 is a flowchart showing an exemplary processing procedure of a method of controlling a support arm device according to the present embodiment.

Also, processes shown in FIG. 7 correspond to the processes performed by the control device 210 of the support arm device 10 illustrated in FIG. 6. That is, when a processor of the control device 210 is operated according to a predetermined program, the processes shown in FIG. 7 are performed. Since details of the processes shown in FIG. 7 have already been described in the above (2. Functional Configuration of Support Arm Device), descriptions of a processing procedure of the following control method are provided in an overview of the processes, and details thereof will be omitted.

As shown in FIG. 7, in a method of controlling the support arm device 10 according to the present embodiment, first, an arm state is acquired based on a state of the joint unit 130 (step S101). Here, the state of the joint unit 130 includes, for example, a rotation angle and a generated torque of the joint unit 130 detected by the joint state detecting unit 132 illustrated in FIG. 6. In addition, the arm state refers to a movement state of the arm unit 110, for example, a position, a speed, an acceleration, and a force of the arm unit 110. Note that, the process shown in step S101 corresponds to the process performed by the arm state acquisition unit 241 illustrated in FIG. 6.

Next, computation conditions corresponding to a plurality of tasks to be performed by the arm unit 110 are set (step S103). In step S103, for example, a plurality of tasks designated by the user and constraint conditions corresponding to the plurality of tasks are set as a computation condition for calculating a control value (the above-described generated torque $\tau_a$) used for driving the arm unit 110 to perform the task. Note that, the process shown in step S103 corresponds to the process performed by the computation condition setting unit 242 illustrated in FIG. 6.

Next, based on the arm state and the computation condition, computation of a general cooperative control using generalized inverse dynamics is performed and the generated torque $\tau_a$ in the joint unit 130 is calculated (step S105). In step S105, first, a virtual force that is necessary to simultaneously perform a plurality of tasks set in step S103 and is applied to each of the joint units 130 of the arm unit 110 is calculated. Next, based on the calculated virtual force, when an actual force that is necessary to simultaneously perform the plurality of tasks set in step S103 and actually applied to each of the joint units 130 of the arm unit 110 is calculated, the generated torque $\tau_a$ in the joint unit 130 is calculated. Note that, the process shown in step S105 corresponds to the process performed by the virtual force calculating unit 243 and the actual force calculating unit 244 illustrated in FIG. 6.

Next, computation of an ideal joint control is performed and the torque command value $\tau$ is calculated from the generated torque $\tau_a$ (step S107). In step S107, specifically, the disturbance estimation value $\tau_d$, which is a torque value due to a disturbance, is calculated, and the disturbance estimation value $\tau_d$ is used to calculate a torque command value, which is a command value indicating a torque that is ultimately generated in the joint unit 130 of the arm unit 110. Note that, the process shown in step S107 corresponds to the process performed by the ideal joint control unit 250 (that is, the disturbance estimating unit 251 and the command value calculating unit 252) illustrated in FIG. 6.

Next, based on the calculated torque command value $\tau$, driving of the joint unit 130 of the arm unit 110 is controlled (step S109). In this case, as the torque command value $\tau$, the torque command value $\tau$ enabling each of the joint units 130 to simultaneously implement the plurality of tasks set in step S103 is calculated. Accordingly, in step S109, when each of the joint units 130 is driven based on the calculated torque command value $\tau$, the arm unit 110 is driven to simultaneously perform the plurality of tasks.

The processing procedure of the method of controlling the support arm device 10 according to the present embodiment has been described above with reference to FIG. 7.

(5. Specific Example of Control Method)

Some tasks will be exemplified to describe the method of controlling the support arm device 10 when a specific task is set. Here, as a specific example, a case in which "ensuring a visual field area" is set as a task and a case in which "avoiding a mechanically limited orientation" is set as a task will be described.

(5-1. When "Ensuring a Visual Field Area" is Set as a Task)

A processing procedure of the method of controlling the support arm device 10 when "ensuring a visual field area" is set as a task will be described with reference to FIG. 8. Here, as an example, a processing procedure in which "maintaining a viewpoint of an imaging unit" is set as a first task, and "ensuring a visual field area" is set as a second task will be described.

FIG. 8 is a flowchart showing an exemplary processing procedure of the method of controlling the support arm device 10 according to the present embodiment when "ensuring a visual field area" is set as a task. Note that, processes shown in FIG. 8 describe the flowchart shown in FIG. 7 in further detail in connection with a specific task of "ensuring a visual field area." That is, the processes shown in FIG. 8 correspond to the processes performed by the control device 210 of the support arm device 10 illustrated in FIG. 6.

As shown in FIG. 8, in the method of controlling the support arm device 10 according to the present embodiment, first, before surgery is performed, processes shown in steps S201 to S205 are performed. The processes shown in steps S201 to S205 correspond to processes of setting a visual field area for performing "ensuring a visual field area." Specifically, in step S201, a position of a monitor that is provided in the operating room and on which a state of the operation part captured by the imaging unit 140 of the support arm device 10 is displayed is set. Next, in step S203, positions of both eyes of the operator who observes the monitor during surgery are set. Then, in step S205, the visual field area is calculated and set based on information on such set positions.

In the present embodiment, the control device 210 of the support arm device 10 may include a calculating unit configured to calculate the visual field area and an acquisition unit configured to acquire information on the visual field area based on a result of the calculation by the calculating unit. The process in the above-described step S205 may be performed by the calculating unit and the acquisition unit.

A process of setting a visual field area will be described in detail with reference to FIG. 9. FIG. 9 is a diagram for describing a process of setting a visual field area.

FIG. 9 illustrates a state in which an operator 501 performs surgery on a patient 505 lying on an operating table 503. While illustration is omitted in order to avoid complicating the drawing, the support arm device 10 illustrated in FIG. 6 is installed in the operating room, and a state of the operation part is captured by the imaging unit 140 of the support arm device 10. A monitor 507 is provided on a wall surface in the operating room, and the state of the operation part captured by the imaging unit 140 is displayed on the monitor 507. The monitor 507 is provided at a position facing the operator 501, and the operator 501 performs the surgery while observing the operation part through the monitor 507.

In this manner, a positional relation among the operator 501, the patient 505 (that is, the operating table 503), and the monitor 507 during the surgery may be substantially constant. That is, the positional relation among the operator 501, the operating table 503 and the monitor 507 in the operating room may be predicted in advance before the surgery.

In the present embodiment, based on such a positional relation predicted in advance, in steps S201 and S203 shown in FIG. 8, a three-dimensional position of the monitor 507 and a three-dimensional position of both eyes of the operator 501 are set in the control device 210 of the support arm device 10. Then, in step S205, the calculating unit of the control device 210 calculates the visual field area based on such positions. Information on the visual field area calculated by the calculating unit is acquired by the acquisition unit, and the acquisition unit sets the visual field area based on the acquired information.

For example, as illustrated in FIG. 9, the visual field area may be calculated as an area 509 of a predetermined range from a line connecting positions of both eyes of the operator 501 and a display surface of the monitor 507 (that is, the area 509 of a cylindrical shape whose center is the line). In steps S201 and S203, since three-dimensional coordinates of the monitor 507 and the both eyes of the operator 501 are set, the control device 210 can calculate the visual field area 509 based on such information. Also, a specific size (that is, a diameter of a cylinder) of the visual field area 509 may be appropriately set in consideration of a field of view range of a general human and a distance between the operator 501 and the monitor 507.

Here, the control device 210 sets the position of the monitor 507, the positions of both eyes of the operator 501, and the visual field area 509 on the same coordinate system as in the internal model used in the drive control of the arm unit 110. That is, the control device 210 sets the position of the monitor 507, the positions of the both eyes of the operator 501, and the position of the visual field area 509 in connection with position information of the arm unit 110. Accordingly, the control device 210 can recognize a positional relation between the set visual field area 509 and the arm unit 110.

Note that, the shape of the visual field area 509 illustrated in FIG. 9 is an example, and the visual field area 509 is not limited thereto. For example, the visual field area 509 may be set as a cone (such as a cone or a triangular pyramid) whose bottom is the display surface of the monitor 507 using a center position between both eyes of the operator 501 as a vertex.

Referring back to FIG. 8, descriptions of the processing procedure of the control method will continue. Processes in steps S207 to S219 to be described below correspond to the specific control method of the arm unit 110 during surgery.

When surgery starts and the operator 501 moves the imaging unit 140 in order to change a viewpoint, a movement of the imaging unit 140 is detected (step S207). Specifically, the process in step S207 corresponds to the process in which a movement of the imaging unit 140 is detected by the joint state detecting unit 132 illustrated in FIG. 6 and the arm state is acquired by the arm state acquisition unit 241.

Next, based on the acquired arm state, it is determined whether the visual field area 509 set in step S205 is not interfered with by the arm unit 110 (that is, any portion of the arm unit 110 does not enter the visual field area 509) (step S209). As described above, since the visual field area 509 is set on the same coordinate system as in the internal model, the control device 210 can decide interference between the visual field area 509 and the arm unit 110.

In step S209, when it is determined that the visual field area 509 is interfered with by the arm unit 110, the process advances to step S211, and the first task (in the illustrated example, "maintaining a viewpoint of an imaging unit") is set. Moreover, the process advances to step S213, and the second task (in the illustrated example, "ensuring a visual field area") is set. Then, a control value (that is, a generated torque in each of the joint units 130) used to implement the plurality of set tasks is calculated and the arm unit 110 is driven based on the calculated control value (step S217).

Here, "setting of a task" in steps S211 and S213 and in step S215 to be described below specifically corresponds to a process of setting r(t) and v(t) in the above-described Expression (2). That is, when it is determined that the visual field area 509 is interfered with by the arm unit 110 in step S209, a variable corresponding to "maintaining a viewpoint of an imaging unit" is set to r(t) in Expression (2) in step S211, and a variable corresponding to "ensuring a visual field area" is set to v(t) in Expression (2) in step S213. Then, a process of calculating a control value in step S217 corresponds to a process in which Expression (2) in which the variables r(t) and v(t) corresponding to the first task and the second task are set in this manner is solved and a rotation angle or the like of each of the joint units 130 is obtained.

Note that, in the process in step S213, for example, based on information on the arm state indicating the state of the arm unit 110 and the visual field area 509, the variable v(t) is set in a manner that a distance between the visual field area 509 and each link of the arm unit 110 is maximized. FIG. 10 is a diagram for describing a distance between a visual field area and an arm unit. FIG. 10 illustrates an arm unit 510 and a visual field area 515 in a simulated manner. While units are illustrated in a simplified manner for simplicity of description, the arm unit 510 corresponds to the arm unit 420 illustrated in FIG. 1 or the arm unit 110 illustrated in FIG. 6, and the visual field area 515 corresponds to the visual field area 509 illustrated in FIG. 9.

In the illustrated example, the arm unit 510 is configured in a manner that ends of a plurality of links 512a, 512b, 512c, and 512d are linked to each other by joint units 511a, 511b, and 511c. In step S213, for example, a length of a vertical line from a center of the visual field area 515 to each of the links 512a to 512d is calculated as a distance between the visual field area 515 and each of the links 512a to 512d, and the variable v(t) is set in a manner that a sum of these distances is maximized. In FIG. 10, as an example, the vertical line from the center of the visual field area 515 to the links 512b and 512c is illustrated. Accordingly, the variable v(t) is set in a manner that the arm unit 510 does not enter the visual field area 515.

On the other hand, in step S209, when it is determined that the visual field area 509 is not interfered with by the arm unit 110, there is no need to consider "ensuring a visual field area" when the drive control of the arm unit 110 is performed (that is, when a control value in each of the joint units 130 is calculated). Accordingly, in this case, the process advances to step S211, and the first task (in the illustrated example, "maintaining a viewpoint of an imaging unit") is set. That is, in Expression (2), a variable corresponding to "maintaining a viewpoint of an imaging unit" is set to r(t), and zero is set to v(t). Then, the process advances to step S217, the control value is calculated based on Expression (2) in which only the variable r(t) corresponding to the first task is set in this manner, and the arm unit 110 is driven based on the control value.

Note that, the processes shown in steps S211, S213, and S215 correspond to the processes performed by the computation condition setting unit 242 illustrated in FIG. 6. In addition, the process shown in step S217 corresponds to the process performed by the virtual force calculating unit 243, the actual force calculating unit 244, the disturbance estimating unit 251, the command value calculating unit 252, and the drive control unit 260 illustrated in FIG. 6.

When the arm unit 110 is driven based on the control value in step S217, it is determined whether the surgery is completed (step S219). When it is determined that the surgery is not completed in step S219, the process returns to step S207, and processes shown in steps S207 to S217 are repeatedly performed. In this manner, during the surgery, the processes shown in steps S207 to S217 are repeatedly performed, for example, every several ms, and driving of the arm unit 110 is controlled at any time. On the other hand, when it is determined that the surgery is completed in step S219, a series of processes according to an arm control is completed.

The processing procedure of the method of controlling the support arm device 10 when "ensuring a visual field area" is set as a task has been described above with reference to FIG. 8.

Here, in the above-described example, while the visual field area 509 is calculated based on the position of the monitor 507 and the positions of both eyes of the operator 501, the present embodiment is not limited thereto. For example, the visual field area 509 may be calculated based on a position and an orientation of the imaging unit 140. In general, in surgery using the video microscope such as the imaging unit 140, in consideration of ease of observation of the operation part by the operator 501, the position and the orientation of the imaging unit 140 are regulated by the operator 501 in many cases (also refer to FIG. 13 to be described below) in a manner that an observation direction when the operator 501 directly observes the operation part and an observation direction (an imaging direction) of the operation part by the imaging unit 140 substantially match (that is, in a manner that a line connecting eyes of the operator 501 and the operation part substantially matches an optical axis of the imaging unit 140). Accordingly, when the position and the orientation of the imaging unit 140 are determined, a position of the operator 501 with respect to the imaging unit 140 may be predicted. In addition, since the operator 501 is highly likely to be positioned in front of the monitor 507, when the position of the operator 501 can be predicted, it is also possible to predict the position of the monitor 507. Accordingly, the calculating unit of the control device 210 calculates the position of the operator 501 and an installation position of the monitor 507 based on the position and the orientation of the imaging unit 140 when the operation part is captured. The acquisition unit may also set the visual field area 509 based on the result. In this manner, the calculating unit of the control device 210 can calculate the visual field area 509 based on at least position information of the support arm device 10.

Alternatively, the visual field area 509 may be appropriately set by the operator according to positions of the support arm device 10 and the monitor 507 in the operating room. In this case, the control device 210 may be configured in a manner that the function of the above-described calculating unit may not be provided in the control device 210, and the acquisition unit acquires information on the visual field area 509 input by the operator through any input device.

In addition, in the above-described example, while the visual field area 509 is calculated and set in advance before the surgery, the present embodiment is not limited thereto. For example, the visual field area 509 may be set at any time during the surgery. For example, a non-contact distance sensor configured to measure a distance between the arm unit 110 and a nearby object may be provided in the arm unit 110, and the control device 210 may estimate a position of the operator 501 corresponding to the arm unit 110 based on a result of the detection by the distance sensor, and set the visual field area 509 according to the estimation result. Alternatively, when an operation field camera configured to image a state of the entire operating room is installed in the operating room, the control device 210 may detect positions of the operator 501 and the monitor 507 based on an image of the operation field camera and set the visual field area 509 according to the detection result. Alternatively, for example, a sensor configured to detect a gaze of the operator 501 may be provided in the monitor 507, and the control device 210 may set the visual field area 509 according to the detection result of the gaze detection sensor. Alternatively, since the surgery is performed while various types of information on the surgery are referred to in real time, a case in which the operator 501 who wears an eyeglass type wearable device or a transmission type head-mounted display (HMD) performs surgery is assumed. In this case, it can be understood that an image of a camera mounted on the wearable device or the HMD represents a field of view (that is, the visual field area 509) of the operator 501. Accordingly, in this case, the control device 210 may set the visual field area 509 based on the image of the camera mounted on the wearable device or the HMD.

Also, in this manner, when the visual field area 509 is set at any time during the surgery, in the method of controlling the support arm device 10, processes shown in steps S201 to S205 are not performed in the flowchart shown in FIG. 8, and a process of setting the visual field area 509 may be performed by the above-described technique in a proceeding stage or a subsequent stage of step S207.

In addition, in the above-described example, while "ensuring a visual field area" is implemented by setting the visual field area 509, the present embodiment is not limited thereto. For example, even when the visual field area 509 is not specifically set, in order to ensure a field of view of the operator, a preferable orientation of the arm unit 110 (hereinafter referred to as a "field of view ensuring orientation") may be set in advance. In "ensuring a visual field area," driving of the arm unit 110 may be controlled in a manner that the arm unit 110 has an orientation that is as close to the field of view ensuring orientation as possible after other tasks are performed. In the field of view ensuring orientation, for example, an orientation may be set in a manner that an elbow position of the arm unit 110 is as low as possible. As illustrated in FIG. 9, when the surgery is performed, since the operator 501 performs a procedure on the operation part below his or her gaze, the field of view of the operator 501 is assumed to be positioned at a relatively high position. Accordingly, when the orientation of the arm unit 110 is controlled in a manner that the elbow position of the arm unit 110 is as low as possible, it is possible to ensure the field of view of the operator 501 even if the visual field area 509 is not specifically set.

In addition, in the above-described example, while "ensuring a visual field area" is implemented by an active control by the control device 210, the present embodiment is not limited thereto. For example, "ensuring a visual field area" may be implemented in a manner that rotation about a redundant axis among axes of rotation of the arm unit 110 is performed according to a manipulation by the operator 501. The manipulation may include a direct manipulation by the operator 501 and a manipulation through the input device such as a foot switch. In the direct manipulation, when an external force other than its own weight is applied, a joint unit corresponding to a redundant axis among the joint units of the arm unit 110 rotates according to the external force, and when no external force is applied, driving thereof may be controlled in a manner that an orientation at that point is maintained. In this case, since driving of the arm unit 110 may be controlled by the force control, it is possible to change the orientation of the arm unit 110 more intuitively in a manner that the arm unit 110 is outside of his or her own field of view through the direct manipulation by the user. In addition, when the manipulation is performed through the input device, the joint unit corresponding to the redundant axis among the joint units of the arm unit 110 may be controlled to be appropriately rotated according to the manipulation through the input device.

Here, in the above description, while "ensuring a visual field area" is a task for only ensuring the visual field area of the operator, the present embodiment is not limited thereto. For example, more generally, "ensuring a visual field area" may be extended to a task of ensuring a work area of the operator. Here, the work area refers to an area according to work of the operator during the surgery, and an area including the operator's hand space for the operator to perform various procedures on the patient in addition to the visual field area. That is, in the present embodiment, in processes according to the above-described "ensuring a visual field area," a wider work area in place of the visual field area may be set. Accordingly, since the arm unit 110 is prevented from interfering with not only the visual field area but also an area of a general work of the operator, for example, the operator's hand space, it is possible for the operator to perform the surgery more smoothly.

(5-2. When "Avoiding a Mechanically Limited Orientation" is Set as a Task)

The method of controlling the support arm device 10 when "avoiding a mechanically limited orientation" is set as a task will be described. Here, as an example, a processing procedure in which "maintaining a viewpoint of an imaging unit" is set as a first task and "avoiding a mechanically limited orientation" is set as a second task will be described.

Even when "avoiding a mechanically limited orientation" is set as the task, similarly to the case in which the above-described "ensuring a visual field area" is set, a variable corresponding to "maintaining a viewpoint of an imaging unit" is set to r(t) and a variable corresponding to "avoiding a mechanically limited orientation" is set to v(t) in Expression (2). Then, the control device 210 solves Expression (2) in which the variables r(t) and v(t) corresponding to the first task and the second task are set in this manner, and calculates a control value in each of the joint units 130. When the control device 210 drives each of the joint units 130 according to the control value, the arm unit 110 is driven in a manner that "maintaining a viewpoint of an imaging unit" and "avoiding a mechanically limited orientation" are implemented together.

In the process of setting the variable v(t) corresponding to "avoiding a mechanically limited orientation," for example, the variable v(t) may be set according to the following Expression (16) in a manner that an evaluation function p(q) shown in the following Expression (15) is minimized.

[Math. 14]

$$p(q) = \sum_{i=1}^{n} \left(\frac{q_i - q_{ci}}{\Delta q_i}\right)^2 \tag{15}$$

$$v = k_0 \nabla p \tag{16}$$

Here, i is a number representing each of the joint units 130, $q_i$ denotes a rotation angle in an i-th joint unit 130, $q_{ci}$ denotes a center value of a movable range of the rotation angle in the i-th joint unit 130, and $\Delta q_i$ denotes the movable range of the rotation angle in the i-th joint unit 130. That is, in the evaluation function p(q) shown in Expression (15), deviations from a center of movable ranges of rotation angles of the joint units 130 are normalized by the movable range, and a sum thereof is obtained. When the evaluation function is used and the variable v(t) is set in a manner that the sum of deviations from the center of movable ranges of rotation angles of the joint units 130 according to Expression (16) is minimized, driving of each of the joint units 130 is controlled not to violate mechanical limitations as much as possible.

Alternatively, as the evaluation function p(q), a function shown in the following Expression (17) may be used in place of the function shown in Expression (15). Even in this case, when the variable v(t) is set according to Expression (16) in a manner that the evaluation function p(q) shown in the following Expression (17) is minimized, the variable v(t) may be set to implement "avoiding a mechanically limited orientation."

[Math. 15]

$$p(q) = \max \frac{|q_i - q_{ci}|}{\Delta q_i} = \left\| \frac{q_i - q_{ci}}{\Delta q_i} \right\|_\infty \quad (17)$$

Here, i, $q_i$, $q_{ci}$, and $\Delta q_i$ are the same as those in Expression (15). That is, in the evaluation function p(q) shown in Expression (17), deviations from a center of movable ranges of rotation angles of the joint units 130 are normalized by the movable range, and a maximum value thereof is obtained. When the evaluation function is used and the variable v(t) is set in a manner that a maximum value of deviations from the center of movable ranges of rotation angles of the joint units 130 according to Expression (16) is minimized, driving of each of the joint units 130 is controlled not to violate mechanical limitations as much as possible.

Also, as shown in the most right-hand side of Expression (17), the evaluation function p(q) may be obtained by calculating a maximum norm (an infinity norm). However, since the maximum norm is unable to be differentiated, when a p norm shown in the following Expression (18) is actually calculated and p is set at an infinite value, the evaluation function p(q) can be obtained. Also, in practice, p is not necessarily set at the infinite value, and p may be around 6.

[Math. 16]

$$\|x\|_p = \left( \sum_{i=1}^n |x_i|^p \right)^{1/p} \quad (18)$$

In this manner, when "avoiding a mechanically limited orientation" is set as the task, a control value of each of the joint units 130 is calculated based on a rotation angle and a movable range of each of the joint units 130, and driving thereof may be controlled.

Here, FIGS. 11 and 12 show experiment results when the inventors actually set "avoiding a mechanically limited orientation" as a task and perform drive control of the arm unit. FIG. 11 is a diagram illustrating a configuration of an arm unit used in an experiment of drive control when "avoiding a mechanically limited orientation" is set as a task. FIG. 12 shows the graph of results of drive control of an arm unit when "avoiding a mechanically limited orientation" is set as a task.

As illustrated in FIG. 11, an arm unit 520 used in the experiment includes a plurality of links 522a, 52b, 522c, 522d, and 522e and the joint units 511a, 511b, 511c, 511d, 511e, and 511f that rotatably connect the plurality of links 522a to 522e.

A configuration of the arm unit 520 will be described in detail. As illustrated, a joint unit 521f having an axis of rotation substantially orthogonal to an extending direction of the link 522e is provided at a leading end of the link 522e that extends in a vertical direction from a floor.

A base end of the link 522d that extends in a direction substantially orthogonal to a direction of an axis of rotation thereof is connected to the joint unit 521f. The joint unit 521f rotatably supports the base end of the link 522d with respect to the link 522e.

A joint unit 521e; having an axis of rotation substantially orthogonal to an extending direction of the link 522d and a direction of the axis of rotation of the joint unit 521f is provided at a leading end of the link 522d.

A base end of the link 522c that extends in a direction substantially orthogonal to a direction of an axis of rotation thereof is connected to the joint unit 521e. The joint unit 521e rotatably supports the base end of the link 522c with respect to the link 522d.

A joint unit 521d having an axis of rotation that is substantially parallel to an axis of rotation of the joint unit 521e is provided at a leading end of the link 522c. Furthermore, a joint unit 521c having an axis of rotation substantially orthogonal to an axis of rotation of the joint unit 521d is provided at the joint unit 521d. The joint unit 521d rotatably supports the joint unit 521c with respect to the link 522c.

A base end of the link 522b that extends in a direction substantially parallel to a direction of an axis of rotation thereof is connected to the joint unit 521c. The joint unit 521c rotatably supports the base end of the link 522b with respect to the joint unit 521d.

The joint unit 521b having an axis of rotation that is substantially parallel to an axis of rotation of the joint unit 521d is provided at a leading end of the link 522b.

A base end of the link 522a that extends in a direction substantially parallel to a direction of an axis of rotation thereof is connected to the joint unit 521b. The joint unit 521b rotatably supports the base end of the link 522a with respect to the link 522b.

A joint unit 521a having an axis of rotation that is substantially parallel to an extending direction of the link 522a is provided at a leading end of the link 522a.

A base end of an imaging unit 523 is connected to the joint unit 521a in a manner that an optical axis substantially parallel to a direction of an axis of rotation thereof is provided. The joint unit 521a rotatably supports the base end of the imaging unit 523 with respect to the link 522a.

In the arm unit 520 having such a configuration, the inventors moved a leading end of the imaging unit 523 to an end point 533 from a start point 531 shown in the drawing when a task of fixing an orientation (that is, a direction of an optical axis of the imaging unit 523) of the imaging unit 523 is set. In this case, when "avoiding a mechanically limited orientation" is or is not set as an additional task, the arm unit 520 is driven, and behaviors of changes in rotation angles of the joint units 521a to 521f when the arm unit 520 is driven are compared. Also, when "avoiding a mechanically limited orientation" is set, the evaluation function p(q) shown in Expression (15) is used and the variable v(t) is set in a manner that a sum of deviations from a center of movable ranges of rotation angles of the joint units 521a to 521f is minimized.

Here, as an example, a change of the rotation angle in the joint unit 521a is illustrated in FIG. 12. In FIG. 12, a horizontal axis represents a time, a vertical axis represents a rotation angle of the joint unit 521a, and a change of the rotation angle over time is plotted when the arm unit 520 is driven. A solid line indicates the result obtained when "avoiding a mechanically limited orientation" is not set, and a dashed line indicates the result obtained when "avoiding a mechanically limited orientation" is set. Also, in FIG. 12, a dashed line indicates +45 degrees that is a mechanical limitation of the rotation angle in the joint unit 521a.

As illustrated in FIG. 12, when "avoiding a mechanically limited orientation" is not set, the rotation angle of the joint unit 521a reaches +45 degrees serving as a limit value. Accordingly, when the operator is assumed to actually manipulate the arm unit 520, the joint unit 521a may not smoothly rotate, and operability of the operator may decrease.

On the other hand, when "avoiding a mechanically limited orientation" is set, the rotation angle of the joint unit 521a does not reach +45 degrees serving as a limit value, and a movement of the imaging unit 523 can be implemented. That is, since the joint unit 521a can be rotated under a movement limit, it is possible to increase operability when the operator moves the imaging unit 523.

The method of controlling the support arm device 10 when "avoiding a mechanically limited orientation" is set as the task has been described above.

Here, in the above-described example, when the variable v(t) corresponding to "avoiding a mechanically limited orientation" is set, the evaluation function p(q) shown in Expression (15) or Expression (17) is set, and v(t) is set based on the evaluation function p(q). However, the present embodiment is not limited thereto. For example, in each of the joint units 130, when a rotation angle thereof is close to the limit of the movable range, v(t) may be set in a manner that a torque in a direction opposite to the rotation angle is generated. Even in this case, the arm unit 110 may be driven in a manner that "avoiding a mechanically limited orientation" is implemented.

(6. Application Example)

A state in which surgery is performed using a support arm device according to the present embodiment will be described with reference to FIG. 13. FIG. 13 is a diagram schematically illustrating a state in which surgery is performed using a support arm device according to the present embodiment.

FIG. 13 schematically illustrates a state in which surgery is performed using the support arm device 400 according to the present embodiment described with reference to FIG. 1. As illustrated in FIG. 13, an operator 701 performs surgery on an operation part of a head of a patient 703 lying on an operating table. The arm unit 420 of the support arm device 400 is installed to be suspended from the ceiling, and an orientation thereof is controlled in a manner that the operation part of the patient 703 is captured by the imaging unit 423 provided at a leading end. The display device (not illustrated) is installed in a direction of the operator 701's gaze. An image of the operation part captured by the imaging unit 423 is displayed on the display device. The operator 701 performs the surgery while referring to the image of the operation part projected on the display device.

In the present application example, for example, "maintaining a viewpoint of an imaging unit" is set as the first task and "ensuring a field of view of an operator" is set as the second task for the support arm device 400. In this case, even when a force is applied to the arm unit 420 from the outside, driving of the arm unit 420 may be controlled in a manner that the position and the orientation of the imaging unit 423 are not changed and a component of the arm unit 420 does not enter the visual field area of the operator 701 set in advance. Accordingly, the surgery is smoothly performed and convenience of the operator 701 increases.

Also, in FIG. 13, a visual field area 705 of the operator 701 is illustrated with hatching in a simulated manner. In the example illustrated in FIG. 13, the visual field area 705 is set as an area having a conical shape whose vertex is the operator 701's eye.

Also, as described in the above (5-1. When "ensuring a visual field area" is set as a task), the task of "ensuring a field of view of an operator" may be implemented by controlling the orientation of the arm unit 420 to be close to the field of view ensuring orientation, or implemented by appropriately changing the orientation of the arm unit 420 by a manipulation of the operator 701.

In this manner, when the first task and the second task are set and driving of the arm unit 420 is controlled in a manner that the first task and the second task are simultaneously implemented, the support arm device 400 having higher convenience is implemented.

The state in which surgery is performed using the support arm device 400 according to the present embodiment has been described above with reference to FIG. 13. Also, a task that may be set for the support arm device 400 during the surgery is not limited to the above-described example. Some of various tasks described in the above (3. Specific Example of Tasks) may be combined with one another (when possible), and set for the support arm device 400.

(7. Supplement)

While exemplary embodiments of the present disclosure have been described above in detail with reference to the accompanying drawings, the scope of the present disclosure is not limited thereto. It should be understood by those skilled in the art that various modifications, combinations, sub-combinations, and alterations may occur depending on design requirements and other factors insofar as they are within the scope of the appended claims or the equivalents thereof.

In addition, the effects described in the present specification are merely illustrative and demonstrative, and not limitative. In other words, the technology according to an embodiment of the present disclosure can exhibit other effects that are evident to those skilled in the art along with or instead of the effects based on the present specification.

Additionally, the present technology may also be configured as below.

(1)

A medical support arm device including:

an observation unit that is used to observe an operation part of a patient;

an arm unit having a leading end at which the observation unit is provided and configured to have a higher degree of freedom than a degree of freedom necessary for controlling a position and an orientation of the observation unit; and a drive control unit configured to control driving of a plurality of joint units of the arm unit, wherein the arm unit is capable of changing an orientation of the arm unit when the position and the orientation of the observation unit are controlled.

(2)

The medical support arm device according to (1), wherein the drive control unit controls the driving of the plurality of joint units according to an external force against the arm unit.

(3)

The medical support arm device according to (1) or (2), wherein the drive control unit controls the driving of the plurality of joint units in a manner that the observation unit performs a pivot operation using a predetermined point in a space as a center when the position and the orientation of the observation unit are controlled.

(4)

The medical support arm device according to any one of (1) to (3), further including:

an acquisition unit configured to acquire information on a work area of an operator, wherein the drive control unit controls the driving of the plurality of joint units in a manner that the arm unit avoids the work area based on an arm state and information on the work area.

(5)

The medical support arm device according to (4), further including:

a calculating unit configured to calculate the work area based on at least position information of the medical support arm device, wherein the acquisition unit acquires the information on the work area based on a result of the calculation by the calculating unit.

(6)

The medical support arm device according to any one of (1) to (5), wherein the observation unit is a video microscope configured to image the operation part of the patient.

(7)

The medical support arm device according to any one of (1) to (6), wherein the observation unit is an endoscope that is inserted into a body cavity of the patient and images the operation part in the body cavity.

(8)

The medical support arm device according to any one of (1) to (7), wherein the drive control unit controls the driving of the plurality of joint units in a manner that the arm unit does not have a specific orientation.

(9)

The medical support arm device according to any one of (1) to (7), wherein the drive control unit controls the driving of the plurality of joint units in a manner that the arm unit does not have a mechanically impractical orientation.

(10)

The medical support arm device according to (9), wherein the drive control unit controls the driving of the plurality of joint units based on a rotation angle and a movable range of the plurality of joint units.

(11)

The medical support arm device according to any one of (1) to (7), wherein the drive control unit controls the driving of the plurality of joint units in a manner that energy consumed when the orientation of the arm unit is changed is minimized.

(12)

The medical support arm device according to any one of (1), to (11), wherein the arm unit is configured by a plurality of links that are linked to each other by the joint units, and wherein, in the arm unit, a joint unit configured to rotate the link of a leading end side about a first axis of rotation substantially parallel to an extending direction of the link of a base end side linked to the joint unit, and a joint unit configured to rotate the link of the leading end side about a second axis of rotation substantially orthogonal to the extending direction of the link of the base end side linked to the joint unit are alternately disposed.

(13)

The medical support arm device according to any one of (1) to (11), wherein the arm unit is configured by a plurality of links that are linked to each other by the joint units, wherein the joint unit is either a joint unit configured to rotate the link of a leading end side about a first axis of rotation substantially parallel to an extending direction of the link of a base end side linked to the joint unit or a joint unit configured to rotate the link of the leading end side about a second axis of rotation substantially orthogonal to the extending direction of the link of the base end side linked to the joint unit, and wherein the joint unit having the second axis of rotation is continuously disposed in at least a part of the arm unit.

(14)

The medical support arm device according to any one of (1) to (13), wherein the arm unit has 7 degrees of freedom or 8 degrees of freedom.

(15)

The medical support arm device according to any one of (1) to (14), wherein, when the driving of the plurality of joint units is controlled to change the position and the orientation of the observation unit and when the driving of the plurality of joint units is controlled to change the orientation of the arm unit, the drive control unit sets a viscosity resistance in a rotating operation of each of the joint units at a different value.

(16)

The medical support arm device according to (15), wherein the viscosity resistance of the joint unit driven to implement control of the position and the orientation of the observation unit is set at a value greater than the viscosity resistance of another joint unit.

(17)

The medical support arm device according to any one of (1) to (16), wherein at least one of axes of rotation corresponding to the joint units corresponds to a driving shaft that is driven by an actuator to rotate, and wherein a remaining axis of rotation among axes of rotation corresponding to the joint units corresponds to a passive shaft that is driven by rotation of the driving shaft to rotate.

(18)

A medical support arm device including:

an observation unit that is used to observe an operation part of a patient;

a holding unit configured to hold the observation unit;

an arm unit provided having a leading end at which the holding unit is provided and configured to have a higher degree of freedom than a degree of freedom necessary for controlling a position and an orientation of the observation unit; and a drive control unit configured to control driving of a plurality of joint units of the arm unit, wherein, in the arm unit, when a position and an orientation of the holding unit are controlled, the position and the orientation of the observation unit are controlled, and wherein the arm unit is configured in a manner that an orientation of the arm unit is changeable when the position and the orientation of the observation unit are controlled.

(19)

A method of controlling a medical support arm device including:

controlling, by a processor, driving of an arm unit, in a manner that an orientation of the arm unit is changeable when a position and an orientation of an observation unit are controlled when driving of a plurality of joint units of the arm unit is controlled, in drive control of the arm unit configured to have a higher degree of freedom than a degree of freedom necessary for controlling the position and the orientation of the observation unit provided at a leading end.

(20)

A medical support arm device including:

a multi-joint arm having a distal end configured to host a medical device, said multi-joint arm configured to have a higher degree of freedom than a degree of freedom necessary for controlling a spatial position and pointing direction of the medical device, wherein the multi-joint arm is configured to controllably displace at least one of a plurality of joints of the multi-joint arm while the spatial position and the pointing direction of the medical device are controlled.

(21)

The medical support arm device according to (20), further including the medical device disposed at the distal end of the multi-joint arm.

(22)

The medical support arm device according to (21), wherein the medical device includes observation optics.

(23)

The medical support arm device according to (22), wherein the observation optics include imaging circuitry that is included in at least one of a video camera or a digital still camera configured to image a part of a patient.

(24)

The medical support arm device according to (21), wherein the medical device includes a surgical tool.

(25)

The medical support arm device according to (20), further including:

a drive controller configured to control a driving of the joints of the multi-joint arm.

(26)

The medical support arm device according to (25), wherein the drive controller is configured to drive at least one of the plurality of joints in response to an external force being applied against the multi-joint arm.

(27)

The medical support arm device according to (26), wherein the drive controller is configured to drive at least one of the plurality of joints so that the medical device performs a pivot operation using a predetermined point in a space as a center.

(28)

The medical support arm device according to (20), further including:

circuitry configured to acquire information on a work area of an operator, wherein the drive controller is configured to drive one or more of the plurality of joints so that the multi-joint arm avoids the work area based on an arm state and information on the work area.

(29)

The medical support arm device according to (28), wherein the circuitry is further configured to calculate the work area based on at least position information of the multi-joint arm, wherein the circuitry acquires the information on the work area based on a result of the calculation by the circuitry.

(30)

The medical support arm device according to (22), wherein the medical device is an endoscope that is inserted into a body cavity of the patient and images an operation site in the body cavity.

(31)

The medical support arm device according to (25), wherein the drive controller is configured to control a driving of the plurality of joints into multiple three dimensional spatial positions.

(32)

The medical support arm device according to (31), wherein the drive controller is configured to control a driving of the plurality of joints based on a rotation angle and a movable range of the plurality of joints.

(33)

The medical support arm device according to (20), wherein the multi-joint arm includes a plurality of links joined by respective of the plurality of joints, in the multi-joint arm, a first joint of the plurality of joints is configured to rotate a link of a distal end side about a first axis of rotation substantially parallel to an extending direction of another link of a base end side linked via the first joint, and a second joint of the plurality of joints is configured to rotate the link of the distal end side about a second axis of rotation substantially orthogonal to the extending direction of the another link of the base end side linked to the second joint, the first joint and the second joint being disposed adjacent to one another.

(34)

The medical support arm device according to (20), wherein the multi-joint arm includes a plurality of links joined by the plurality of joints, respective of the plurality of joints being a joint configured rotate a link of a distal end side about a first axis of rotation substantially parallel to an extending direction of a link of a base end side linked to the joint or a joint configured to rotate the link of the distal end side about a second axis of rotation substantially orthogonal to the extending direction of the link of the base end side linked to the joint, and the joint having the second axis of rotation being disposed in at least a part of the multi-joint arm.

(35)

The medical support arm device according to (20), wherein the multi-joint arm has 7 degrees of freedom or 8 degrees of freedom.

(36)

The medical support arm device according to (20), wherein when the drive controller drives the plurality of joints to change the spatial position and the pointing direction of the medical device, the drive controller sets a viscosity resistance in a rotating operation of each of the joints at a different value.

(37)

The medical support arm device according to (36), wherein the viscosity resistance of a joint driven to position and orient the medical device is applied at a value greater than the viscosity resistance of another joint.

(38)

The medical support arm device according to (20), wherein at least one of axes of rotation corresponding to the joints corresponds to a driving shaft that is driven by an actuator to rotate, and wherein a remaining axis of rotation among axes of rotation corresponding to the joints corresponds to a passive shaft that is driven by rotation of the driving shaft to rotate.

(39)

A medical support arm device including:

a medical device configured to assist in a medical procedure on a patient;

a multi-joint arm having a distal end to which the medical device is disposed configured to have a higher degree of freedom than a degree of freedom necessary for controlling a spatial position and a pointing direction of the medical device; and a drive controller configured to control a driving of a plurality of joint units of the multi-joint arm, wherein in the multi-joint arm, when a spatial position and a pointing direction of the distal end of the multi-joint arm is controlled, the spatial position and the orientation of the medical device are controlled, and the multi-joint arm is configured to change a pointing direction and a spatial position of the multi-joint arm when the spatial position and the pointing direction of the medical device are controlled.

(40)

A method of controlling a medical support arm device including:

controlling, by processing circuitry, driving of a multi-joint arm to that a spatial position and a pointing direction of the multi-joint arm is changeable when a spatial position and a pointing direction of a medical device are controlled when driving of a plurality of joints of the multi-joint arm are controlled, wherein movement of the multi-joint arm has a higher degree of freedom than a degree of freedom necessary for controlling the spatial position and the pointing direction of the medical device provided at a distal end of the multi-joint arm.

REFERENCE SIGNS LIST 1 observation system
10, 400 support arm device
30 display device
110, 420 arm unit
130, 421a, 421b, 421c, 421d, 421e, 421f, 421g, 421h joint unit
131 joint drive unit
132 joint state detecting unit
133 rotation angle detecting unit
140, 423 imaging unit
210, 440 control device
240 general cooperative control unit
241 arm state acquisition unit
242 computation condition setting unit
243 virtual force calculating unit
244 actual force calculating unit
250 ideal joint control unit
251 disturbance estimating unit
252 command value calculating unit
260 drive control unit 422a, 422b, 422c, 422d, 422e, 422f, 422g, 422h link
430 actuator
424, 611 motor
425 motor driver
426, 612 decelerator
427, 613 encoder
428, 614 torque sensor

The invention claimed is:

1. A medical support arm device comprising:
   a multi joint arm having a distal end configured to host a medical device, said multi-joint arm configured to have a higher degree of freedom than a degree of freedom necessary for controlling a spatial position and a pointing direction of the medical device; and
   control circuitry configured to
   set a visual field area between an operator and a display, and
   displace at least one of a plurality of joints of the multi-joint arm so that the multi-joint arm avoids the visual field area while the spatial position and the pointing direction of the medical device are controlled.

2. The medical support arm device according to claim 1, further comprising
   the medical device disposed at the distal end of the multi joint arm.

3. The medical support arm device according to claim 2, wherein
   the medical device includes observation optics.

4. The medical support arm device according to claim 3, wherein
   the observation optics include imaging circuitry that is included in at least one of a video camera or a digital still camera configured to image a part of a patient.

5. The medical support arm device according to claim 2, wherein
   the medical device includes a surgical tool.

6. The medical support arm device according to claim 1,
   wherein the control circuitry is configured to control a driving of the joints of the multi-joint arm.

7. The medical support arm device according to claim 6, wherein
   the control circuitry is configured to drive at least one of the plurality of joints in response to an external force being applied against the multi joint arm.

8. The medical support arm device according to claim 7, wherein
   the control circuitry is configured to drive at least one of the plurality of joints so that the medical device performs a pivot operation using a predetermined point in a space as a center.

9. The medical support arm device according to claim 6, wherein
   the control circuitry is configured to control a driving of the plurality of joints into multiple three dimensional spatial positions.

10. The medical support arm device according to claim 9, wherein
    the control circuitry is configured to control a driving of the plurality of joints based on a rotation angle and a movable range of the plurality of joints.

11. The medical support arm device according to claim 1, wherein:
    the control circuitry is further configured to acquire information on a work area of the operator, and
    to drive one or more of the plurality of joints so that the multi joint arm avoids the work area based on an arm state and the information on the work area, the work area being larger than the visual field area.

12. The medical support arm device according to claim 11, wherein
the control circuitry is further configured to calculate the work area based on at least position information of the multi joint arm.

13. The medical support arm device according to claim 1, wherein the medical device is an endoscope that is inserted into a body cavity of a patient and images an operation site in the body cavity.

14. The medical support arm device according to claim 1, wherein
the multi joint arm includes a plurality of links joined by respective of the plurality of joints, and
in the multi-joint arm, a first joint of the plurality of joints is configured to rotate a link of a distal end side about a first axis of rotation substantially parallel to an extending direction of another link of a base end side linked via the first joint, and
a second joint of the plurality of joints is configured to rotate the link of the distal end side about a second axis of rotation substantially orthogonal to the extending direction of the another link of the base end side linked to the second joint, the first joint and the second joint being disposed adjacent to one another.

15. The medical support arm device according to claim 1, wherein
the multi-joint arm includes a plurality of links joined by the plurality of joints, respective of the plurality of joints being a joint configured rotate a link of a distal end side about a first axis of rotation substantially parallel to an extending direction of a link of a base end side linked to the joint or a joint configured to rotate the link of the distal end side about a second axis of rotation substantially orthogonal to the extending direction of the link of the base end side linked to the joint, and
the joint having the second axis of rotation being disposed in at least a part of the multi-joint arm.

16. The medical support arm device according to claim 1, wherein
the multi-joint arm has 7 degrees of freedom or 8 degrees of freedom.

17. The medical support arm device according to claim 1, wherein
in a case that the control circuitry is to drive the plurality of joints to change the spatial position and the pointing direction of the medical device, the control circuitry is configured to set a viscosity resistance in a rotating operation of each of the joints at a different value.

18. The medical support arm device according to claim 17, wherein
the viscosity resistance of a joint driven to position and orient the medical device is applied at a value greater than the viscosity resistance of another joint.

19. The medical support arm device according to claim 1, wherein
at least one of axes of rotation corresponding to the joints corresponds to a driving shaft that is driven by an actuator to rotate, and
wherein a remaining axis of rotation among axes of rotation corresponding to the joints corresponds to a passive shaft that is driven by rotation of the driving shaft to rotate.

20. A medical support arm device comprising:
a medical device configured to be used in a medical procedure on a patient;
a multi joint arm having a distal end to which the medical device is disposed configured to have a higher degree of freedom than a degree of freedom necessary for controlling a spatial position and a pointing direction of the medical device; and
control circuitry configured to
control a driving of a plurality of joint units of the multi-joint arm,
set a visual field area between an operator and a display, and
displace at least one of a plurality of joints of the multi-joint arm so that the multi-joint arm avoids the visual field area while the spatial position and the pointing direction of the medical device are controlled, wherein
in the multi joint arm, when a spatial position and a pointing direction of the distal end of the multi joint arm is controlled, the spatial position and the orientation of the medical device are controlled, and
the multi joint arm is configured to change a pointing direction and a spatial position of the multi joint arm when the spatial position and the pointing direction of the medical device are controlled.

21. A method of controlling a medical support aim device comprising:
controlling, by processing circuitry, driving of a multi joint arm to that a spatial position and a pointing direction of the multi joint arm is changeable when a spatial position and a pointing direction of a medical device are controlled when driving of a plurality of joints of the multi-joint arm are controlled, wherein movement of the multi-joint arm has a higher degree of freedom than a degree of freedom necessary for controlling the spatial position and the pointing direction of the medical device provided at a distal end of the multi-joint arm;
setting a visual field area between an operator and a display; and
displacing at least one of a plurality of joints of the multi-joint arm so that the multi-joint arm avoids the visual field area while the spatial position and the pointing direction of the medical device are controlled.

* * * * *